(12) United States Patent
Fulga et al.

(10) Patent No.: US 8,685,724 B2
(45) Date of Patent: Apr. 1, 2014

(54) IN VITRO TECHNIQUES FOR USE WITH STEM CELLS

(75) Inventors: Valentin Fulga, Toronto (CA); Yael Porat, Hod Hasharon (IL); Danny Belkin, Givat Shmuel (IL); Daphna Shimoni-Zalk, Nes Ziona (IL); Svetlana Porozov, Rehovot (IL)

(73) Assignee: Kwalata Trading Limited, Nicosia (CY)

( * ) Notice: Subject to any disclaimer, the term of this patent is extended or adjusted under 35 U.S.C. 154(b) by 899 days.

(21) Appl. No.: 11/628,488

(22) PCT Filed: Jun. 1, 2005

(86) PCT No.: PCT/IL2005/000571
§ 371 (c)(1),
(2), (4) Date: Mar. 24, 2008

(87) PCT Pub. No.: WO2005/120090
PCT Pub. Date: Dec. 15, 2005

(65) Prior Publication Data
US 2008/0220466 A1    Sep. 11, 2008

Related U.S. Application Data

(60) Provisional application No. 60/576,266, filed on Jun. 1, 2004, provisional application No. 60/588,520, filed on Jul. 15, 2004.

(51) Int. Cl.
*C12N 15/00* (2006.01)

(52) U.S. Cl.
USPC .......................................... 435/325; 435/372

(58) Field of Classification Search
USPC .................................. 435/325, 372
See application file for complete search history.

(56) References Cited

U.S. PATENT DOCUMENTS

| | | | |
|---|---|---|---|
| 3,411,507 A | 11/1968 | Wingrove | |
| 3,774,243 A | 11/1973 | Ng et al. | |
| 3,837,339 A | 9/1974 | Aizenbreg et al. | |
| 3,837,922 A | 9/1974 | Ng et al. | |
| 3,861,397 A | 1/1975 | Rao et al. | |
| 4,019,518 A | 4/1977 | Maurer et al. | |
| 4,090,921 A | 5/1978 | Swamura et al. | |
| 4,140,963 A | 2/1979 | Rao et al. | |
| 4,161,952 A | 7/1979 | Kinney et al. | |
| 4,338,945 A | 7/1982 | Kosugi et al. | |
| 4,344,438 A | 8/1982 | Schultz | |
| 4,352,883 A | 10/1982 | Lim | |
| 4,392,496 A | 7/1983 | Stanton | |
| 4,402,694 A | 9/1983 | Ash et al. | |
| 4,535,785 A | 8/1985 | Van Den Honert et al. | |
| 4,559,948 A | 12/1985 | Liss et al. | |
| 4,573,481 A | 3/1986 | Bullara | |
| 4,578,323 A | 3/1986 | Hersl et al. | |
| 4,585,005 A | 4/1986 | Lue et al. | |
| 4,602,624 A | 7/1986 | Naples et al. | |
| 4,608,985 A | 9/1986 | Chrish et al. | |
| 4,628,942 A | 12/1986 | Sweeney et al. | |
| 4,632,116 A | 12/1986 | Rosen | |
| 4,640,785 A | 2/1987 | Carroll et al. | |
| 4,649,936 A | 3/1987 | Ungar et al. | |
| 4,663,102 A | 5/1987 | Brenman et al. | |
| 4,696,902 A | 9/1987 | Bisconte | |
| 4,702,254 A | 10/1987 | Zabara | |
| 4,721,677 A | 1/1988 | Clark, Jr. | |
| 4,739,764 A | 4/1988 | Lue et al. | |
| 4,867,164 A | 9/1989 | Zabara | |
| 4,883,755 A | 11/1989 | Carabasi et al. | |
| 4,926,865 A | 5/1990 | Oman | |
| 4,962,751 A | 10/1990 | Krauter | |
| 4,966,853 A | 10/1990 | Matsuda et al. | |
| 4,981,779 A | 1/1991 | Wagner | |
| 5,001,054 A | 3/1991 | Wagner | |
| 5,011,472 A | 4/1991 | Aebischer et al. | |
| 5,025,807 A | 6/1991 | Zabara | |
| 5,042,497 A | 8/1991 | Shapland | |
| 5,069,680 A | 12/1991 | Grandjean | |
| 5,089,697 A | 2/1992 | Prohaska | |

(Continued)

FOREIGN PATENT DOCUMENTS

| WO | WO87/06223 | 10/1987 |
|---|---|---|
| WO | WO 87/06233 | 10/1987 |

(Continued)

OTHER PUBLICATIONS

Martin et al. "Gradient separation of granulocytic progenitor cells (CFUc) from human blood mononuclear leukocytes", Exp. Hematol. 1985, 13:79-86.*

(Continued)

*Primary Examiner* — Bin Shen
(74) *Attorney, Agent, or Firm* — Nixon Peabody LLP; David S. Resnick; Leena H. Karttunen Contarino

(57) ABSTRACT

A method is provided for use with extracted blood, including (a) applying blood to a first gradient suitable for selecting first-pass cells having a density less than 1.077 g/ml; (b) applying the first-pass cells to a second gradient suitable for selecting second-pass cells having a density between 1.055 and 1.074 g/ml; (c) increasing the number of cells having a density between 1.055 and 1.074 g/ml, by culturing the second-pass cells for a period lasting between 3 and 30 days; and (d) identifying endothelial progenitor cells in the cultured cells. Other embodiments are also described.

10 Claims, 1 Drawing Sheet

(56) References Cited

U.S. PATENT DOCUMENTS

| | | |
|---|---|---|
| 5,101,814 A | 4/1992 | Palti |
| 5,116,494 A | 5/1992 | Chick et al. |
| 5,170,802 A | 12/1992 | Mehra |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker |
| 5,209,231 A | 5/1993 | Cote et al. |
| 5,215,086 A | 6/1993 | Terry et al. |
| 5,224,491 A | 7/1993 | Mehra |
| 5,243,980 A | 9/1993 | Mehra |
| 5,246,867 A | 9/1993 | Lakowicz et al. |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry et al. |
| 5,356,425 A | 10/1994 | Bardy et al. |
| 5,368,028 A | 11/1994 | Palti |
| 5,381,075 A | 1/1995 | Jordan |
| 5,411,531 A | 5/1995 | Hill et al. |
| 5,423,872 A | 6/1995 | Cigaina |
| 5,424,209 A | 6/1995 | Kearney |
| 5,427,935 A | 6/1995 | Wang et al. |
| 5,437,285 A | 8/1995 | Verrier et al. |
| 5,439,938 A | 8/1995 | Snyder et al. |
| 5,443,508 A | 8/1995 | Giampapa |
| 5,454,840 A | 10/1995 | Krakovsky et al. |
| 5,473,706 A | 12/1995 | Bac et al. |
| 5,487,756 A | 1/1996 | Kallesoe et al. |
| 5,507,784 A | 4/1996 | Hill et al. |
| 5,522,854 A | 6/1996 | Ideker et al. |
| 5,529,066 A | 6/1996 | Palti |
| 5,540,730 A | 7/1996 | Terry et al. |
| 5,540,734 A | 7/1996 | Zabara |
| 5,562,718 A | 10/1996 | Palermo |
| 5,571,150 A | 11/1996 | Wernicke et al. |
| 5,578,061 A | 11/1996 | Stroetmann et al. |
| 5,614,378 A | 3/1997 | Yang et al. |
| 5,626,134 A | 5/1997 | Zuckerman |
| 5,634,462 A | 6/1997 | Tyler et al. |
| 5,645,570 A | 7/1997 | Corbucci |
| 5,658,318 A | 8/1997 | Stroetmann et al. |
| 5,660,940 A | 8/1997 | Larsson et al. |
| 5,690,681 A | 11/1997 | Geddes et al. |
| 5,690,691 A | 11/1997 | Chen |
| 5,700,282 A | 12/1997 | Zabara |
| 5,702,444 A | 12/1997 | Struthers et al. |
| 5,707,400 A | 1/1998 | Terry et al. |
| 5,711,316 A | 1/1998 | Elsberry et al. |
| 5,716,385 A | 2/1998 | Mittal et al. |
| 5,741,334 A | 4/1998 | Mullon et al. |
| 5,755,750 A | 5/1998 | Petruska et al. |
| 5,770,454 A | 6/1998 | Essenpreis et al. |
| 5,824,027 A | 10/1998 | Hoffer et al. |
| 5,832,932 A | 11/1998 | Elsberry et al. |
| 5,833,709 A | 11/1998 | Rise et al. |
| 5,834,005 A | 11/1998 | Usala |
| 5,836,994 A | 11/1998 | Bourgeois |
| 5,840,502 A | 11/1998 | Van Vlasselaer |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 5,916,239 A | 6/1999 | Geddes et al. |
| 5,938,584 A | 8/1999 | Ardito et al. |
| 5,980,887 A | 11/1999 | Isner et al. |
| 5,985,653 A | 11/1999 | Armstrong et al. |
| 5,998,204 A | 12/1999 | Tsien et al. |
| 6,006,134 A | 12/1999 | Hill et al. |
| 6,026,326 A | 2/2000 | Bardy |
| 6,048,721 A | 4/2000 | Armstrong et al. |
| 6,049,727 A | 4/2000 | Crothall |
| 6,058,331 A | 5/2000 | King et al. |
| 6,061,582 A | 5/2000 | Small et al. |
| 6,066,163 A | 5/2000 | John |
| 6,066,497 A | 5/2000 | Powell |
| 6,073,048 A | 6/2000 | Kieval et al. |
| 6,086,525 A | 7/2000 | Davey et al. |
| 6,091,974 A | 7/2000 | Palti |
| 6,091,977 A | 7/2000 | Tarjan et al. |
| 6,091,992 A | 7/2000 | Bourgeois |
| 6,093,531 A | 7/2000 | Bjornson et al. |
| 6,094,598 A | 7/2000 | Elsberry et al. |
| 6,096,532 A | 8/2000 | Armstrong et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| H1905 H | 10/2000 | Hill |
| 6,127,141 A | 10/2000 | Kopf |
| 6,134,470 A | 10/2000 | Hartlaub |
| 6,146,335 A | 11/2000 | Gozani |
| 6,161,029 A | 12/2000 | Spreigl et al. |
| 6,163,714 A | 12/2000 | Stanley et al. |
| 6,167,304 A | 12/2000 | Loos |
| 6,169,924 B1 | 1/2001 | Meloy et al. |
| 6,188,477 B1 | 2/2001 | Pu et al. |
| 6,197,534 B1 | 3/2001 | Lakowicz et al. |
| 6,205,359 B1 | 3/2001 | Boveja |
| 6,228,635 B1 | 5/2001 | Armstrong et al. |
| 6,230,061 B1 | 5/2001 | Hartung |
| 6,238,908 B1 | 5/2001 | Armstrong et al. |
| 6,240,314 B1 | 5/2001 | Plicci et al. |
| 6,254,601 B1 | 7/2001 | Burbank et al. |
| 6,261,832 B1 | 7/2001 | Law |
| 6,266,564 B1 | 7/2001 | Hill et al. |
| 6,272,377 B1 | 8/2001 | Sweeney et al. |
| 6,292,695 B1 | 9/2001 | Webster, Jr. et al. |
| 6,294,281 B1 | 9/2001 | Heller |
| 6,319,241 B1 | 11/2001 | King et al. |
| 6,341,236 B1 | 1/2002 | Osorio et al. |
| 6,352,555 B1 | 3/2002 | Dzau et al. |
| 6,356,784 B1 | 3/2002 | Lozano et al. |
| 6,366,813 B1 | 4/2002 | Dilorenzo |
| 6,368,592 B1 | 4/2002 | Colton et al. |
| 6,381,499 B1 | 4/2002 | Taylor et al. |
| 6,400,974 B1 | 6/2002 | Lesho |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler et al. |
| 6,463,328 B1 | 10/2002 | John |
| 6,473,644 B1 | 10/2002 | Terry, Jr. et al. |
| 6,493,585 B2 | 12/2002 | Plicci et al. |
| 6,511,500 B1 | 1/2003 | Rahme |
| 6,521,446 B2 | 2/2003 | Hellinga |
| 6,542,774 B2 | 4/2003 | Hill et al. |
| 6,564,096 B2 | 5/2003 | Mest |
| 6,569,428 B1 | 5/2003 | Isner et al. |
| 6,577,393 B1 | 6/2003 | Potzschke et al. |
| 6,587,704 B1 | 7/2003 | Fine et al. |
| 6,587,727 B2 | 7/2003 | Osorio et al. |
| 6,600,956 B2 | 7/2003 | Maschino et al. |
| 6,602,251 B2 | 8/2003 | Burbank et al. |
| 6,605,039 B2 | 8/2003 | Houben et al. |
| 6,610,713 B2 | 8/2003 | Tracey |
| 6,625,479 B1 | 9/2003 | Weber et al. |
| 6,628,987 B1 | 9/2003 | Hill et al. |
| 6,630,154 B1 | 10/2003 | Fraker et al. |
| 6,650,919 B1 | 11/2003 | Edelberg et al. |
| 6,668,191 B1 | 12/2003 | Boveja |
| 6,671,556 B2 | 12/2003 | Osorio et al. |
| 6,673,595 B2 | 1/2004 | Barbera-Guillem |
| 6,676,937 B1 | 1/2004 | Isner et al. |
| 6,684,105 B2 | 1/2004 | Cohen et al. |
| RE38,525 E | 6/2004 | Stanley et al. |
| 6,764,488 B1 | 7/2004 | Burbank et al. |

(56) References Cited

U.S. PATENT DOCUMENTS

| | | |
|---|---|---|
| 6,767,737 B1 | 7/2004 | Wilson et al. |
| 6,780,617 B2 | 8/2004 | Chen |
| 6,790,654 B2 | 9/2004 | Malinge |
| 6,810,286 B2 | 10/2004 | Donovan et al. |
| 6,846,288 B2 | 1/2005 | Nagar et al. |
| RE38,705 E | 2/2005 | Hill et al. |
| 6,865,416 B2 | 3/2005 | Dev et al. |
| 6,895,280 B2 | 5/2005 | Meadows et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,015,037 B1 | 3/2006 | Furcht et al. |
| 7,050,846 B2 | 5/2006 | Sweeney et al. |
| 7,068,867 B2 | 6/2006 | Adoram et al. |
| 7,076,299 B2 | 7/2006 | Thong |
| 7,184,810 B2 | 2/2007 | Caduff et al. |
| 2002/0025469 A1 | 2/2002 | Heller |
| 2002/0035335 A1 | 3/2002 | Schauerte |
| 2002/0038083 A1 | 3/2002 | Houben et al. |
| 2002/0107553 A1 | 8/2002 | Hill et al. |
| 2002/0120304 A1 | 8/2002 | Mest |
| 2002/0151056 A1 | 10/2002 | Sasai et al. |
| 2003/0018367 A1 | 1/2003 | Dilorenzo |
| 2003/0040774 A1 | 2/2003 | Terry et al. |
| 2003/0045909 A1 | 3/2003 | Gross et al. |
| 2003/0050677 A1 | 3/2003 | Gross et al. |
| 2003/0078623 A1 | 4/2003 | Weinberg et al. |
| 2003/0087427 A1 | 5/2003 | Colton et al. |
| 2003/0100924 A1 | 5/2003 | Foreman et al. |
| 2003/0134346 A1 | 7/2003 | Amiss et al. |
| 2003/0148512 A1 | 8/2003 | Fanslow et al. |
| 2003/0166271 A1 | 9/2003 | Chen-Bettecken |
| 2003/0195574 A1 | 10/2003 | Osorio et al. |
| 2003/0216759 A1 | 11/2003 | Burbank et al. |
| 2003/0216775 A1 | 11/2003 | Hill et al. |
| 2003/0229380 A1 | 12/2003 | Adams et al. |
| 2003/0232370 A1 | 12/2003 | Trifiro |
| 2003/0233129 A1 | 12/2003 | Matos |
| 2003/0236558 A1 | 12/2003 | Whitehurst et al. |
| 2004/0001807 A1 | 1/2004 | Edelberg et al. |
| 2004/0048375 A1 | 3/2004 | Alt |
| 2004/0048795 A1 | 3/2004 | Ivanova et al. |
| 2004/0059392 A1 | 3/2004 | Parramon et al. |
| 2004/0091757 A1 | 5/2004 | Wang et al. |
| 2004/0097788 A1 | 5/2004 | Mourlas et al. |
| 2004/0109302 A1 | 6/2004 | Yoneda et al. |
| 2004/0126879 A1 | 7/2004 | Schneider et al. |
| 2004/0136973 A1 | 7/2004 | Huberman et al. |
| 2004/0138721 A1 | 7/2004 | Osorio et al. |
| 2004/0138822 A1 | 7/2004 | Rambau |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0199210 A1 | 10/2004 | Shelchuk |
| 2004/0215289 A1 | 10/2004 | Fukui |
| 2004/0228847 A1 | 11/2004 | Goldschmidt et al. |
| 2004/0228897 A1 | 11/2004 | Zhang et al. |
| 2004/0243182 A1 | 12/2004 | Cohen et al. |
| 2004/0249416 A1 | 12/2004 | Yun et al. |
| 2005/0003534 A1 | 1/2005 | Huberman et al. |
| 2005/0113852 A1 | 5/2005 | Burbank et al. |
| 2005/0118726 A1 | 6/2005 | Schultz et al. |
| 2005/0131467 A1 | 6/2005 | Boveja |
| 2005/0187584 A1 | 8/2005 | Denker et al. |
| 2005/0209556 A1 | 9/2005 | Tresco et al. |
| 2005/0222644 A1 | 10/2005 | Killian et al. |
| 2005/0260158 A1 | 11/2005 | Huberman et al. |
| 2005/0272152 A1 | 12/2005 | Xu et al. |
| 2006/0000479 A9 | 1/2006 | Burbank et al. |
| 2006/0015153 A1 | 1/2006 | Gliner et al. |
| 2006/0052831 A1 | 3/2006 | Fukui |
| 2006/0074450 A1 | 4/2006 | Boveja |
| 2006/0129205 A1 | 6/2006 | Boveja et al. |
| 2007/0004974 A1 | 1/2007 | Nagar et al. |
| 2007/0066877 A1 | 3/2007 | Arnold et al. |

FOREIGN PATENT DOCUMENTS

| | | |
|---|---|---|
| WO | WO 90/15526 | 12/1990 |
| WO | WO 91/09312 | 6/1991 |
| WO | WO 98/19712 | 5/1998 |
| WO | WO 01/50983 | 1/2001 |
| WO | 0130981 | 5/2001 |
| WO | WO 01/94420 | 12/2001 |
| WO | WO 03/010303 | 2/2003 |
| WO | WO 03/011445 | 2/2003 |
| WO | WO 03/016507 | 2/2003 |
| WO | WO 03/018760 | 3/2003 |
| WO | WO 03/023022 | 3/2003 |
| WO | WO 03/055989 | 7/2003 |
| WO | WO 03/078610 | 9/2003 |
| WO | WO 03/090512 | 11/2003 |
| WO | WO 2004/028358 | 4/2004 |
| WO | WO 2004/051774 | 6/2004 |
| WO | WO 2004/055989 | 7/2004 |
| WO | WO 2004/089465 | 10/2004 |
| WO | WO 2005/053523 | 6/2005 |
| WO | WO 2005/078073 | 8/2005 |
| WO | 2005120090 | 12/2005 |
| WO | WO 2005/120090 | 12/2005 |
| WO | WO 2006/006166 | 1/2006 |
| WO | WO 2006/064504 | 6/2006 |
| WO | WO 2006/097933 | 9/2006 |
| WO | WO 2007/102162 | 9/2007 |
| WO | WO 2008/018079 | 2/2008 |

OTHER PUBLICATIONS

Dooley et al. "Granulocyte-Monocyte progenitor cells from human peripheral blood: modulation of growth in vitro by T lymphocytes and monocytes", International Journal of Cell Cloning, 1988, 6:45-59.*

Graziani-Bowering et al. "A quick, easy and inexpensive method for the isolation of human peripheral blood monocytes", Journal of Immunological Methods, 1997, 207:157-168.*

Chau et al. "Effect of L-phenylalanine methyl ester on the colony formation of hematopoietic progenitor cells from human bone marrow", International Journal of Cell Cloning, 1991, 9:211-219.*

Ficoll definition: 2 pages. download 2011.*

Andrews et al. "Enrichment of fetal nucleated cells from maternal blood: model test system using cord blood", Prenatal Diagnosis, 1995, 15:913-919.*

BD technical Data Sheet (2003) pp. 1-4.*

Pertoft "Fractionation of cells and subcellular particles with Percoll", Journal of Biochem and Biophy. Methods, 2000, 44:1-30.*

Orlic D, et al., (2001b) "Mobilized Bone Marrow Cells Repair the Infarcted Heart, Improving Function and Survival" *Proc. NatlAcad. Sci. USA* 98, 10344.

Asahara T, et al., (1997) "Isolation of Putative Progenitor Endothelial Cells for Angiogenesis" *Science* 275:964-67.

Norol F, et al., (2003) "Influence of Mobilized Stem Cells on Myocardial in Farctrepair in a Nonhuman Primate Model" *Blood* 102, 4361.

Seiler C, et al., (2001) "Promotion of Collateral Growth by Granulocyte-Macrophage Colony-Stimulating Factor in Patients With Coronary Artery Disease: A Randomized, Double-Blind, Placebo-Controlled Study" *Circulation* 104, 2012.

Toma C, et al., (2002) "Human Mesenchymal Stem Cells Differentiate to a Cardiomyocyte Phenotype in the Adult Murine Heart" *Circulation* 105, 93.

Gojo S, et al., (2003) "In Vivo Cardiovasculogenesis by Direct Injection of Isolated Adult Mesenchymal Stem Cells" *Exp. Cell Res. 288*, 51.

Davani S, et al., (2003) "Mesenchymal Progenitor Cells Differentiate Into an Endothelial Phenotype, Enhance Vascular Density, and Improve Heart Function in a Rat Cellular Cardiomyoplasty Model" *Circulation* 108, II253.

(56) References Cited

OTHER PUBLICATIONS

Badorff C, et al., (2003) "Transdifferentiation of Blood-Derived Human Adult Endothelial Progenitor Cells Into Functionally Active Cardiomyocytes" *Circulation* 107, 1024.
Asahara T, et al., (1999) "Bone Marrow Origin of Endothelial Progenitor Cells Responsible for Postnatal Vasculogenesis in Physiological and Pathological Neovascularization" *Circ. Res.* 85:221-28.
Kocher A.A, et al., (2001) "Neovascularization of Ischemic Myocardium by Human Bone Marrow-Derived Angioblasts Prevents Cardiomyocyte Apoptosis, Reduces Remodeling and Improves Cardiac Function" *Nat. Med.* 7:430-36.
Kalka C, et al., (2000) "VEGF Gene Transfer Mobilizes Endothelial Progenitor Cells in Patients With Inoperable Coronary Disease" *Ann. Thorac. Surg.* 70:829-34.
Shintani S, et al., (2001) "Mobilization of Endothelial Progenitor Cells in Patients With Acute Myocardial Infarction" *Circulation* 103:2776-79.
Takahashi T, et al., "1999) Ischemia- and Cytokine-Induced Mobilization of Bone Marrow-Derived Endothelial Progenitor Cells for Neovascularization" *Nat. Med.* 5:434-38.
Harrison, J.S., et al., (2002) "Oxygen Saturation in the Bone Marrow of Healthy Volunteers" *Blood* 99, 394.
Ceradini D, et al., (2004) "Progenitor Cell Trafficking Is Regulated by Hypoxic Gradients Through Hef-1 Induction of Sdf-1" *Nature Med* 10:858-864.
Penn M.S et al., (2004) "Role of stem cell homing in myocardial regeneration," *International Journal of Cardiology* 95 Suppl. 1:S23-S25.
Franz W.M et al, (2003) "Stem-cell homing and tissue regeneration in ischaemic cardiomyopathy," *The Lancet* 362:675-676.
Payne A.G, (2004) "Using immunomagnetic technology and other means to facilitate stem cell homing," *Medical Hypotheses* 62:718-720.
U.S. Appl. No. 60/631,098, filed Nov. 24, 2004.
U.S. Appl. No. 60/780,781, filed Mar. 8, 2006.
Yael Porat, et al., (2006) "Isolation of an Adult Blood-Derived Progenitor Cell Population Capable of Differentiation Into Angiogenic, Myocardial and Neural Lineages" *British Journal of Haematology* 135, 703-714.
Quesenberry P.J., et al., (2004) "Stem Cell Plasticity: An Overview" *Blood Cells, Molecules, and Diseases* 32 1-4.
Hristov M., et al., (2004) "Adoptotic Bodies From Endothelial Cells Enhance the Number and Initiate the Differentiation of Human Endothelial Progenitor Cells in Vitro" *Blood first Ed. paper*, DOI 10.1182/blood-2003-10-3614.
Forbes S.J., et al., (2002) "Adult Stem Cell Plasticity: New Pathways of Tissue Regeneration Become Visible", *Clinical Science* 103, 355-369.
Shen Q., et al., (2004) "Endothelial Cells Stimulate Self-Renewal and Expand Neurogenesis of Neural Stem Cells" *Science* vol. 34.
Condorelli G., et al., (2001) "Cardiomyocytes Induce Endothelial Cells to Trans-Differentiate Into Cardiac Muscle: Implications for Myocardium Regeneration" *PNAS* vol. 98 No. 19, 10733-10738.
Dimmeler S., et al. (2001) "HMG-Coa Reductase Inhibitors (Statins) Increase Endothelial Progenitor Cells Via the PI 3-Kinase/Akt Pathway" *J. Clin. Invest.* 108: 391-397.
Hyun-Jae, Hyo-Soo Kim, et al. (2003) "Effects of Intracoronary Infusion of Peripheral Blood Stem-Cells Mobilized With Granulocyte-Colony Stimulating Factor on Left Ventricular Systolic Function and Restenosis After Coronary Stenting in Myocardial Infraction: The MAGIC Cell Randomized Clinical Trial" *The Lancet* 363: 751-756.
Brigit Assmus, Volker Schachinger et al., (2002) "Transplantation of Progenitor Cells and Regeneration Enhancement in Acute Myocardial Infraction (TOPCARE-AMI)" *Circulation* 106: 3009-3017.
Alexandra Aicher, Winfreid Brenner, et al., (2003) "Assessment of the Tissue Distribution of Transplanted Human Endothelial Progenitor Cells by Radioactive Labeling" *Circulation* 107: 2134-2139.

Kalka, C, H. Masuda, et al., (2000) "Vascular Endothelial Growth Factor( 165) Gene Transfer Augments Circulating Endothelial Progenitor Cells in Human Subjects" *Circ Res* 86 (12): 1198-202.
Kawamoto, A., H. C. Gwon, et al., (2001) "Therapeutic Potential of Ex Vivo Expanded Endothelial Progenitor Cells for Myocardial Ischemia" *Circulation* 103(5): 634-7.
Kawamoto, A., T. Tkebuchava, et al., (2003) "Intramyocardial Transplantation of Autologous Endothelial Progenitor Cells for Therapeutic Neovascularization of Myocardial Ischemia" *Circulation* 107(3): 461-8.
Kamihata, H., H. Matsubara, et al. (2001) "Implantation of Bone Marrow Mononuclear Cells Into Ischemic Myocardium Enhances Collateral Perfusion and Regional Function Via Side Supply of Angioblasts, Angiogenic Ligands, and Cytokines" *Circulation* 104(9): 1046-52.
Kocher, A.A., M. D. Schuster, et al., (2001) "Neovascularization of Ischemic Myocardium by Human Bone-Marrow-Derived Angioblasts Prevents Cardiomyocyte Apoptosis, Reduces Remodeling and Improves Cardiac Function" *Nat. Med.* 7(4): 430-6.
Flammera, J. et al., (2002) "The Impact of Ocular Blood Flow in Glaucoma" *Progress in Retinal and Eye Research* 21:359-393.
Frank, R.N. (2004) "Diabetic Retinopathy" *N. Engl. J. Med.* 350:48-58.
Singleton, J.R. (2003) "Microvascular Complications of Impaired Glucose Tolerance" *Diabetes* 52:2867-2873.
Bahlmann, F.H. et al., (2004) "Erythropoietin Regulates Endothelial Progenitor Cells" *Blood* 103(3):921-6.
Kouwenhoven, E.A. et al., (2000) "Etiology and Pathophysiology of Chronic Transplant Dysfunction" *Transplant Internat.* 13(6):385-401.
Chen et al., (1991) "Four Types of Venous Flaps for Wound Coverage: A Clinical Appraisal" *J. Trauma* 31(9): 1286-93.
Beatrice R.A., et al., (2004) "Microangiopathy of Split-Skin Grafts in Venous Ulcers" *Dermatol. Surg.* 30(3):399.
Ferretti et al., (2003) "Angiogenesis and Nerve Regeneration in a Model of Human Skin Equivalent Transplant" *Life Sci.* 73:1985-94.
Schechner et al. (2003). "Engraftment of a vascularized human skin equivalent." FASEBJ. 17(15):2250-60.
Perin, E., et al. (2003) "Transendocardial, Autologous Bone Marrow Cell Transplantation for Severe, Chronic Ischemic Heart Failure" *Circulation* 107(18): 2294-302.
Stamm, C, Bet al. (2003) "Autologous Bone-Marrow Stem-Cell Transplantation for Myocardial Regeneration" *Lancet* 361(9351): 45-6.
Amit Patel of University of Pittsburgh. Abstract from American Association for Thoracic Surgery, Toronto, May 2004.
Folkman J., et al., (1992) "Angiogenesis" *J. Biol. Chem.* 267, 10931.
Katz F., et al., (1985) "Identification of a Membrane Glycoprotein Associated With Haemopoietic Progenitor Cells" *Leuk. Res.* 9, 191.
Andrews R.G., et al., (1986) "Monoclonal Antibody 12-8 Recognizes a 115-kd Molecule Present on Both Unipotent and Multipotent Hematopoietic Colony-Forming Cells and Their Precursors" *Blood* 67, 842.
Terman B.I., et al., (1992) "Identification of the KDR Tyrosine Kinase As Receptor for Vascular Endothelial Cell Growth Factor" *Biochem. Biophys. Res. Commun.* 187,1579.
Millauer B., et al., (1993) "High Affinity VEGF Binding and Developmental Expression Suggest Flk-1 As a Major Regulator of Vasculogenesis and Angiogenesis" *Cell* 72, 835.
Newman P.J., et al., (1990) "PECAM-1 (CD31) Cloning and Relation to Adhesion Molecules of the Immunoglobulin Gene Superfamily" *Science* 247, 1219.
Sato T.N., et al., (1995) "Distinct Roles of the Receptor Tyrosine Kinases Tie-1 and Tie-2 in Blood Vessel Formation" *Nature* 376, 70.
Schnurch H., et al., (1993) "Expression of Tie-2, A Membrane of a Novel Family of Receptor Tyrosine Kinases, in the Endothelial Cell Lineage" *Development* 119, 957.
Liesveld J. L., et al., (1994) "Characterization of the Adherence of Normal and Leukemic CD34+ Cells to Endothelial Monolayers" *Leukemia* 8, 2111.
Takeshita S., et al., (1994) "Therapeutic Angiogenesis" *J. Clin. Invest.* 93, 662.

(56) References Cited

OTHER PUBLICATIONS

Baffour R., et al., (1992) "Enhanced Angiogenesis and Growth of Collaterals by In Vivo Administration of Recombinant Basic Fibroblast Growth Factor in a Rabbit Model of Acute Lower Limb Ischemia: Dose-Response Effect of Fibroblast Growth Factor" *J. Vasc. Surg.* 16, 181.
Isner J. M., et al., (1996) "Clinical Evidence of Angiogenesis After Arterial Gene Transfer of phVEGF in Patient With Ischaemic Limb" *Lancet* 348, 370.
Sato Y., et al., (1993) "Idispensable Role of Tissue-Type Plasminogen Activator in Growth Factor-Dependent Tube Formation of Human Microvascular Endothelial Cells In Vitro" *Exp. Cell Res.* 204,223.
Badorff C, et al., (2003) "Transdifferentiation of Blood-Derived Human Adult Endothelial Progenitor Cells Into Functionally Active Cardiomyocytes" *Circulation* 107(7): 1024-32.
Bhattacharya et al., (2000) "Enhanced Endothelialization and Microvessel Formation in Polyester Grafts Seeded With CD34(+) Bone Marrow Cells" *Blood* 95(2): 581-5.
Grant M. B., et al., (2002) "Adult Hematopoietic Stem Cells Provide Functional Hemangioblast Activity During Retinal Neovascularization" *Nat Med* 8(6): 607-12.
Hirata K., et al., (2003) "Autologous Bone Marrow Cell Implantation As Therapeutic Angiogenesis for Ischemic Hindlimb in Diabetic Rat Model" *Am J Physiol Heart Circ Physiol* 284(1): H66-70.
Ikenaga S., et al., (2001) "Autologous Bone Marrow Implantation Induced Angiogenesis and Improved Deteriorated Exercise Capacity in a Rat Ischemic Hindlimb Model" *J Surg Res* 96(2): 277-83.
Kalka C, et al., (2000) "Transplantation of Ex Vivo Expanded Endothelial Progenitor Cells for Therapeutic Neovascularization" *Proc Natl Acad Sci USA* 97(7): 3422-7.
Kaushal S., et al., (2001) "Functional Small-Diameterneovessels Created Using Endothelial Progenitor Cells Expanded Ex Vivo" *Nat Med* 7(9): 1035-40.
Kornowski R., M. B. Leon, et al., (2000) "Electromagnetic guidance for catheter-based transendocardial injection: a platform for intramyocardial angiogenesis therapy. Results in normal and ischemic porcine models." J Am Coll Cardiol 35(4): 1031-9.
Li R. K., et al., (1996) "Cardiomyocyte Transplantation Improves Heart Function" *Ann Thorac Surg* 62(3): 654-60.
Rajnoch C, J. C. Chachques, et al. (2001). "Cellular Therapy Reverses Myocardial Dysfunction" *J Thorac Cardiovasc Surg* 121(5): 871-8.
Schatteman G. C, et al., (2000) "Blood-Derived Angioblasts Accelerate Blood-Flow Restoration in Diabetic Mice" *J Clin Invest* 106(4): 571-8.
Shintani S., et al., (2001) "Augmentation of Postnatal Neovascularization With Autologous Bone Marrow Transplantation" *Circulation* 103(6): 897-903.
Strauer B. E., M. Brehm, etal. (2002) "Repair of Infarcted Myocardium by Autologous Intracoronary Mononuclear Bone Marrow Cell Transplantation in Humans" *Circulation* 106(15): 1913-8.
Taylor D. A., et al., (1998) "Regenerating Functional Myocardium: Improved Performance After Skeletal Myoblast Transplantation" *Nat Med* 4(8): 929-33.
Thompson C. A., et al., (2003) "Percutaneous Transvenous Cellular Cardiomyoplasty. A Novel Nonsurgical Approach for Myocardial Cell Transplantation" *J Am Coll Cardiol* 41(11): 1964-71.
Tomita S., et al., (1999) "Autologous Transplantation of Bone Marrow Cells Improves Damaged Heart Function" *Circulation* 100(19 Suppl): 11247-56.
Tomita S., et al. (2002) "Improved Heart Function With Myogenesis and Angiogenesis After Autologous Porcine Bone Marrow Stromal Cell Transplantation" *J Thorac Cardiovasc Surg* 123(6): 1132-40.
Wang et al., (2004) "Rosiglitazone Facilitates Angiogenic Progenitor Cell Differentiation Toward Endothelial Lineage: A New Paradigm in Glitazone Pleiotropy" *Circulation* 109(11): 1392-400.
Rupp et al., (2004) "Statin Therapy in Patients With Coronary Artery Disease Improves the Impaired Endothelial Progenitor Cell Differentiation Into Cardiomyogenic Cells" *Basic Res Cardiol*. 99(1): 61-8.

Quirici et al., (2001) "Differentiation and Expansion of Endothelial Cells From Human Bone Marrow CD133(+) Cells" *Br J Haematol*. 115(1): 186-94.
Di Stefano et al., (2002) "Different Growth Conditions for Peripheral Blood Endothelial Progenitors" *Cardiovasc Radiat Med*. 3(3-4): 172-5.
Akita et al., (2003) "Hypoxic Preconditioning Augments Efficacy of Human Endothelial Progenitor Cells for Therapeutic Neovascularization" *Lab Invest*. 83(1): 65-73.
Wang et al., (2004) "Mechanical, Cellular, and Molecular Factors Interact to Modulate Circulating Endothelial Cell Progenitors" *Am J Physiol Heart Circ Physiol*. 286(5): H1985-93.
Bahlmann et al., (2003) "Endothelial Progenitor Cell Proliferation and Differentiation Is Regulated by Erythropoietin" *Kidney Int*. 64(5): 1648-52.
Heeschen et al., (2003) "Erythropoietin Is a Potent Physiologic Stimulus for Endothelial Progenitor Cell Mobilization" *Blood*. 102(4): 1340-6.
Verma et al., (2004) "C-Reactive Protein Attenuates Endothelial Progenitor Cell Survival, Differentiation, and Function: Further Evidence of a Mechanistic Link Between C-Reactive Protein and Cardiovascular Disease" *Circulation*. 109(17): 2058-67.
Asahara T, et al., (1999) "VEGF Contributes to Postnatal Neovascularization by Mobilizing Bone Marrow-Derived Endothelial Progenitor Cells" *EMBO J*. 18:3964-72 *Circulation* 107:3059-65.
Zhang ZG, et al., (2002) "Bone Marrow-Derived Endothelial Progenitor Cells Participate in Cerebral Neovascularization After Focal Cerebral Ischemia in the Adult Mouse" *Circ. Res*. 90:284-88.
Gill M, et al., (2001) "Vascular Trauma Induces Rapid But Transient Mobilization Ofvegfr2+AC133+ Endothelial Precursor Cells" *Circ. Res*. 88:167-74.
Hao H.N., et al., (2003) "Fetal Human Hematopoeietic Stem Cells Can Differentiate Sequentially Into Neural Stem Cells and Then Astrocytes In Vito" *J. Hematother Stem Cell Res*. 12:23-32.
Jarrell B.E., et al., (1986) "Use of an Endothelial Monolayer on a Vascular Graft Prior to Implantation" *Ann. Surg*. 671-8.
Williams S.K, et al., (1985) "Adult Human Endothelial Cell Compatibility With Prosthetic Graft Material" *Journal of Surgical Research* 38:618-629.
Hur, Jin et al., (2004) "Characterization of two types of endothelial progenitor cells and their different contributions to neovasculogenesis," *Arteriosclerosis, Thrombosis, and Vascular Biology*, 24(2): 288-293.
Kocher, A.A., (2006) "Myocardial homing and neovascularization by human bone marrow angioblasts is regulated by IL-8/Gro CXC chemokines," Abstract only, *Journal of Molecular and Cellular Cardiology*, 40(2):455-464.
Office Action issued in corresponding JP Application No. 2009-514327 issued on Aug. 30, 2011.
Asahara, et al., Science, vol. 275, pp. 964-967, 1997.
Repnik, et al., Journal of Immunological Methods, vol. 278, pp. 283-292, 2003.
Urbich, et al., Circulation, vol. 108, pp. 2511-2516, 2003.
Slack J.M.W., Science, 287:1431-1433 (2000). "Stem cells in epithelial tissues."
Spradling et al., Nature, 414:98-104. (Nov. 1, 2001).
Stock et al., Ann Rev Med, 52:443-451 (2001). "Tissue engineering: current state and prospects."
Theise et al., Hepatology, 32:11-16 (2000). "Live from bone marrow in humans."
Tolosa et al., Sensors and Acuators, B45:93-99 (1997). "Optical assay for glucose based on the luminescence decay time of the long wavelength dye Cy5."
Urbich et al., Circulation Research, 95:343-353 (2004). Endothelial progenitor cells: characterization and role in vascular biology.
Challen, et al., PLos One, vol. 3, Issue 6; 1-9 (2008). "Promiscuous Expression of H2B-GFP Transgene in Hematopoietic Stem Cells."
Vecchi et al., Eur J Cell Biol, 63:247-254 (1994). "Monoclonal antibodies specific for endothelial cells of mouse blood vessels. Their application in the identification of adult and embryonic endothelium."

(56) References Cited

OTHER PUBLICATIONS

Steidl, et al. Blood, 104: 81-88 (2004). "Primary human CD34+ hematopoietic stem and progenitor cells express functionally active receptors of neuromediators."
Wagers et al., Science, 297:2256-2259 (2002). "Little evidence for developmental plasticity of adult hematopoietic stem cells."
Wan et al., Chin Med J (Engl), 116(3):428-431 (2003). "Differentiation of rat embryonic neural stem cells promoted by co-cultured Schwann cells."
Ward, Drug Discovery World, 33-38 (2003). "Automating cell culture to optimise cell line generation and selection."
Weimann et al., PNAS USA, 100:2088-2093 (2003). "Contribution of transplanted bone marrow cells to purkinje neurons in human adult brains."
Weissman et al., Annu Rev Cell Dev Biol, 17:387-403 (2001). "Stem and progenitor cells: origins, phenotypes, lineage commitments, and transdifferentiations."
Weissman, Cell, 100:157-68 (2000). "Stem, cells: unit of development, units of regeneration, and units in evolution."
Written Opinion of the International Searching Authority issued by the International Searching Authority (ISA/US) on May 15, 2007 in connection with International Application No. PCT/IL2005/001345.
Wulf et al., Exp Hematol, 29:1361-1370 (2001). "Somatic stem cell plasticity."
Yamamoto et al., J. Appl Physiol, 95:2081-2088 (2003). "Proliferation, differentiation, and tube formation by endothelial progenitor cells in response to shear stress."
Yeh et al., Circulation, 108(17):2070-2073 (2003). "Transdifferentiation of human peripheral blood CD34+ enriched cell population into cardiomyocytes, endothelial cells, and smooth muscle cells in vivo."
Yoon et al., Circulation, 112:1618-1627 (2005). "Synergistic neovascularization by mixed transplantation of early endothelial progenitor cells and late outgrowth endothelial cells, the role of angiogenic cytokines and matrix metalloproteinases."
Zhao et al., Exp Neurol, 174:11-20 (2002). "Human bone marrow stem cells exhibit neural phenotypes and ameliorate neurological deficits grafting into the ischemic brain of rats." Abstract Only.
Zhao et al., PNAS USA, 100(5):2426-2431 (2003). "A human peripheral blood monocyte-derived subset acts as pluripotent stem cells."
Zhang et al., Circ Res, 90:284-288 (2002). "Bone marrow-derived endothelial progenitor cells participate in cerebral neovascularization after focal cerebral ischemia in the adult mouse."
Fulga et al., U.S. Appl. No. 60/576,266, published Dec. 15, 2005.
Fulga et al., U.S. Appl. No. 60/588,520, published Dec. 15, 2005.
Porat et al., U.S. Appl. No. 60/636,391, published Jun. 22, 2006.
Porat, U.S. Appl. No. 60/668,739, published Jun. 22, 2006.
Belkin et al., U.S. Appl. No. 60/687,115, published Jul. 12, 2006.
Examination Report issued Nov. 6, 2009 in connection with European Patent Application No. 05745232.8.
Response dated May 12, 2010 to European Examination Report in connection with European Application No. 05745232.8.
Supplementary Search Report issued Aug. 27, 2008 in connection with European Patent Application No. 05745232.8.
Examination Report issued Nov. 19, 2010 in connection with European Patent Application No. 05745232.8.
Response dated Jun. 18, 2009 to European Examination Report in connection with European Application No. 05745232.8.
Hunt et al., Current Opinion in Biotechnology, 20:522-530 (2009). "Multipotent skin-derived precursors: from biology to clinical translation."
International Preliminary Report on Patentability issued by the International Bureau of WIPO dated Jun. 19, 2007 in connection with International Application No. PCT/IL2005/001345.
International Search Report issued by the International Searching Authority (ISA/US) on May 15, 2007 in connection with International Application No. PCT/IL2005/001345.
Jackson et al., J Clin Invest, 107(11):1395-1402 (2001). "Regeneration of ischemic cardiac muscle and vascular endothelium by adult stem cells."
Jackson et al., PNAS USA, 96:25:14482-14486 (1999). "Hemaopoietic potential of stem cells isolated from murine skeletal muscle."
Jang et al., Nat Cell Biol, 6(6):532-539 (Epub May 9, 2004). "Hematopoietic stem cells convert into liver cells within days without fusion."
Kanayasu-Toyoda et al., J Cell Physiol, 195:119-129 (2003). "CD31 (PECAM-1) bright cells derived from AC133-positive cells in human peripheral blood as endothelial-precursor cells."
Fernandes et al., Nature Cell Biology, published online Nov. 10, 2004: DOI: 10.1038/ncbl 181 (2004). "A dermal niche for multipotent adult skin-derived precursor cells."
Kayisli et al., J Clin Endocrinol Metab, 89:5794-5802 (2004). "Regulation of angiogenic activity of human endometrial endothelial cells in culture by ovarian steroids."
Kim et al., Plast Reconstr Surg, 94:580-584 (1994). "Bone defect repair with tissue-engineered cartilage."
Kleeberger et al., Hepatology, 35:110-116 (2002). "High frequency of epithelial chimerism in liver transplants demonstrated by microdissection and STR-analysis."
Kollet et al., J Clin Invest, 112(2):160-169 (2003). "HGF, SDF-1, and MMP-9 are involved in stress-induced human CD34+ stem cell recruitment to the liver."
Krause, D.S., Gene Ther, 9:754-758 (2002). "Plasticity of marrow-derived stem cells."
Kubota et al., Cell Transplantation, 12(6):647-657 (2003). "Transplanted endothelial progenitor cells augment the survival areas of rat dorsal flaps."
Lagasse et al., Immunity, 14:425-436 (2001). "Toward regenerative medicine."
Lagasse et al., Nat Med, 6:1229-1234 (2000). "Purified hematopoietic stem cells can differentiate into hepatocytes in vivo."
Laterveer et al., Blood, 85(8):2269-2275 (1995). "Interleukin-8 induces rapid mobilization of hematopoietic stem cells with radioprotective capacity and long-term myelolymphoid repopulating ability."
Leblond, C.P., Natl Cancer Inst Monogr, 14:119-150 (1964). "Classification of cell populations on the basis of their proliferative behavior."
Li et al., J Cereb Blood Flow Metab, 20:1311-1319 (2000). "Intrastriatal transplantation of bone marrow nonhematopoietic cells improves functional recovery after stroke in adult mice."
Li et al., J Immunol, 170:3369-3376 (2003). "IL-8 directly enhanced endothelial cell survival, proliferation, and matrix metalloproteinases production and regulated angiogenesis."
Li et al., Neurology, 56:1666-1672 (2001a). "Treatment of stroke in rat with intracarotid administration of marrow stromal cells." Abstract Only.
Li et al., Neurosci Lett, 316:67-69 (2001b). "Intracerebral transplantation of bone marrow stromal cells in a 1-methyl-4-phenyl-1-,2,3,6-tetrahydropyridine mouse model of Parkinson's Disease." Abstract Only.
Liechty et al., Nature Med, 6(11):1282-1286 (2000). "Human mesenchymal stem cells engraft and demonstrate site-specific differentiation after in utero transplantation in sheep."
Liouterman et al., p. 632 (2001). Transplantation of human hematopoietic stem cells in rat brain: analysis of cell survival and Abstract only.
Mahmood et al., Neurosurgery, 49:1196-1203 (2001). "Treatment of traumatic brain injury in female rats with intravenous administration of bone marrow stromal cells." Abstract Only.
Metcalf et al., Journal of Cellular Physiol., 78(1):441-450 (1971). "Adherence column and buoyant density separation of bone marrow stem cells and more differentiated cells."
Mezey et al., Science, 290(5497):1779-1782 (2000). "Turning blood into brain: cells bearing neuronal antigens generated in vivo from bone marrow."
Murry et al., Nature, 428: 664-668 (2004). "Hematopoietic stem cells do not transdifferentiate into cardiac myocytes in myocardial infarcts."

(56) References Cited

OTHER PUBLICATIONS

Newman, J Clin Invest, 99(1):3-8 (1997). "The biology of PECAM-1 perspective series: cell adhesion in vascular biology."

Nishida et al., N Engl J Med, 351:1187-1196 (2004). "Corneal reconstruction with tissue-engineered cell sheets composed of autologous oral mucosal epithelium."

Nygren et al., Nature Medicine, 10(5):494-501 (2004). "Bone marrow-derived hematopoietic cells generate cardiomyocytes at a low frequency through cell fusion but not transdifferentiation."

Office Action issued Mar. 30, 2010 in connection with U.S. Appl. No. 11/820,975, filed Jun. 20, 2007.

Office Action issued May 17, 2010 in connection with U.S. Appl. No. 11/820,991, filed Jun. 20, 2007.

Office Action issued Sep. 15, 2010 in connection with U.S. Appl. No. 11/820,975, filed Jun. 20, 2007.

Ortiz-Gonzalez et al., Current Neurovascular Research, 1(3):207-213 (2004). "Neural induction of adult bone marrow and umbilical cord stem cells."

Petite et al., Nature Biotechnol, 18:959-963 (2000). "Tissue-engineered bone regeneration."

Pittenger et al., Science, 284:143-147 (1999). "Multilineage potential of adult human mesenchymal stem cells."

Price, et al., "Multipotent Adult Progenitor Cell Lines Originating from the Peripheral Blood of Green Fluorescent Protein Transgenic Swine", Stem Cells and Development 15:507-522 (2006).

Priller et al., J Cell Biol, 155(5):733-738 (2001b). "Neogenesis of cerebellar purkinje neurons from gene-marked bone marrow cells in vivo."

Priller et al., Nat Med, 7(12):1356-1361 (2001a). "Targeting gene-modified hematopoietic cells to the central nervous system: Use of green fluorescent protein uncovers microglial engraftment."

Quaini et al., N Engl Med, 346(1):5-15 (2002). "Chimerism of the transplanted heart."

Rafii, S. and Lyden, D., Nature Medicine, 9(6):702-712 (2003). "Therapeutic stem and progenitor cell transplantation for organ vascularization and regeneration."

Ramiya et al., Nature Medicine, 6(3):278-282 (2000). "Reversal of insulin-dependent diabetes using islets generated in vitro from pancreatic stem cells."

Rehman et al., Journal of the American College of Cardiology, 43(12):2314-2318 (2004). "Exercise acutely increases circulating endothelial progenitor cells and monocyte-/macrophage-derived angiogenic cells."

Reinecke et al., J Mol Cell Cardiology, 34, 241-249 (2002).

Robey, P.G., J Clin Invest, 105(11):1489-1491 (2000). "Stem cells near the century mark."

Rodda et al., Int J Dev Biol, 46(4):449-458 (2002). "Embryonic stem cell differentiation and the analysis of mammalian development."

Schomig et al., Eur Heart J, 27:1032-1037 (2006). "Interleukin-8 is associated with circulating CD133+ progenitor cells in acute myocardial infarction."

Shim et al., Biochemical and Biophysical Research Communications, Academic Press Inc., 324(2):481-488 (2004). "Ex vivo differentiation of human adult bone marrow stem cells into cardiomyocyte-like cells."

Akiyoama et al., Neuroscience, 22:6623-6630 (2002). "Remyelination of the rat spinal cord by transplantation of identified bone marrow stromal cells."

Amit et al., Dev Biol, 227(2)1271-278 (2000). "Clonally derived human embryonic stem cell lines maintain pluripotency and proliferative potential for prolonged periods of culture."

Anderson et al., Nat Med, 7:393-395 (2001) "Can stem cells cross lineage boundaries?"

OptiPrep TM Reports, Issue No. 3, 2000.

Aoki et al., Cell Struct Funct, 28(1):55-60 (2003). "Culture of endothelial cells and mature adipocytes activtely promotes immature preadipocyte development in vitro."

Bianco et al., Nature, 414:118-121 (2001) "Stem cells in tissue engineering".

Biernaskie et al., Nature Protocols, 1(6): 2803-12 (2006). "Isolation of skin-derived precursors (SKPs) and differentiation and enrichment of their schwann cell progency."

Bittner et al., Anat Embryol, 199:391-396 (1999), "Recruitment of bone-marrow derived cells by skeletal and cardiac muscle in adult dystrophic MDX mice."

Bjornson et al., Science, 283(5401):534-537 (1999). "Turning brain into blood: a hematopoietric fate adopted by adult neural stem cells in vivo."

Blau et al., Cell, 105:829-841 (2001). The evolving concept of a stem cell: entity or function?.

Bonilla et al., Eur J Neurosci, 15:575-582 (2002), "Haematopoietic progenitor cells from adult bone marrow differentiate into cells that express oligodendroglial antigens in the neonatal mouse brain." Abstract Only.

Brazelton et al., Science, 290(5497):1775-1779 (2000), "From marrow to brain: expression of neuronal phenotypes in adult mice."

Cao et al., Cancer, 91(12):2205-2213 (2001), "Rapid engraftment after allogenetic transplantation of density-enriched peripheral blood CD34+ cells in patients with advanced ehmatologic malignncies."

Castro et al., Science, 2 (5585):1299 (2002). "Failure of bone marrow cells to transdifferentiate into neural cells in vivo."

Chen et al., Stroke, 32:1005-1011 (2001). "Therapeutic benefit of intravenous administration of bone marrow stromal cells after cerebral ischemia in rats."

Cheng et al., Dev Biol, 258(2):319-33 (2003). "Nitric oxide acts in a positive feedback loop with BDNF to regulate neural progenitor cell proliferation cell proliferation and differentiations in the mammalian brain."

Cohen, and Leor, Scientific American, 45-51 (2004). "Rebuilding broken hearts."

Corti et al., Exp Neurol, 177:443-452 (2002). "Modulated generation of neuronal cells from bone marrow by expansion and mobilization of circulating stem cells with in vivo cytokine treatment." Abstract Only.

Cousin et al., Biochem Biophys Res Commun, 301(4):1016-22 (2003). "Reconstitution of lethally irradiated mice by cells isolated from adipose tissue."

Delisser et al., Am J Pathol, 151(3):671-677 (1997). "Involvement of endothelial PECAM-1/CD31 in Angiogenesis."

Dimmeler, S., Blood, 106(7):2231-2232 (2005). "Circulating endothelial precursors: identification of functional subpopulations."

Donovan, P.J. and Gearhart, J., Nature, 414:92-97 (2001). "The end of the beginning for pluripotent stem cells."

Losordo D.W. and Dimmeler, S., Circulation, 109:2487-2491 (2004). "Therapeutic angiogenesis and vasculogenesis for ischemic diseases. Part I: angiogenic cytokines."

Losordo D.W. and Dimmeler, S., Circulation, 109:2692-2697 (2004). "Therapeutic angiogenesis and vasculogenesis for ischemic diseases. Part II: Cell-based therapy."

Eglitis et al., Neuroreport, 10:1289-1292 (1999). "Targeting of marrow-derived astrocytes to the ischemic brain," Abstract Only.

Eglitis,M.A. and Mezey, E., PNAS USA, 94:4080-4085 (1997). "Hematopoietic cells differentiation into both microglia and macroglia in the brains of adult mice."

Eisenberg at al., Anatomical Record Part A, 274A(1):870-832 (2003), "Hematopoietic cells from bone marrow have the potential to differentiate into cardiomyocytes in vitro."

European Examination Report issued Dec. 21, 2009—European Patent Application No. 05817711.

European Examination Report issued Nov. 18, 2008—European Patent Application No. 05817711.

European Search Report issued Aug. 4, 2008—European Patent Application No. 05817711.

European Search Report Issued Jan. 11, 2011—European Patent Application No. 10 190450.

Evans, M.J. and Kaufman, M.H., Nature, 292:154-156 (1981), "Establishment in culture of pluipotential cells from mouse embryos."

Examination Report dated Nov. 3, 2008—European Patent Application No. 05 81 7653.

Examination Report dated Nov. 30, 2009—European Patent Application No. 05 81 7653.

(56) References Cited

OTHER PUBLICATIONS

Examination Report issued Dec. 8, 2008 in connection with European Patent Application No. 05 745 232.8.
Examination Report issued Oct. 8, 2010—EP Patent Application No. 05 817 711.4.
Examination Report issued Sep. 30, 2010—European Patent Application No. 05 817 653.8.
Examiner's first report on Australian Patent Application No. 2006253728, dated Sep. 22, 2010.
Extended European Search Report dated Jul. 30, 2008, which issued during prosecution of European Patent Application No. 05 81 7653.
Ferrari et al., Science, 279:528-530 (1998). "Muscle regeneration by bone marrow-derived myogenic progenitors."
Ferrero et al., p. 123b (2001), "Mobilised peripheral blood progenitor cells give rise in vitro to cells expressing neuronal phenotype."
Gazitt et al., Stem Cells, 19(2):134-143 (2001). "Expression of adhesion molecules on CD34+ cells in peripheral blood of non-Hodgkin's lymphomia patients mobilized with different growth factors."
Goodell et al., Ann NY Acad Sci,938:208-220 (2001). "Stem cell plasticity in muscle and bone marrow."
Goolsby et al., PNAS USA, 100(25):14926-14931 (2003). "Hematopoietic progenitors express neural genes."
Gussoni et al., Nature, 401:390-394 (1999), "Dystrophin expression in the MDX mouse restored by stem cell transplantation."
Hershfinkel et al., PNAS USA, 98:1749-1754 (2001). "A zinc-sensing receptor triggers the release of intracellular Ca2+ and regulates ion transport."
Hess et al., Stroke, 33:1362-1368 (2002). "Bone marrow as a source of endothelial cells and neuN-expressing cells after stroke."
Hirschi et al., Gene Therap, 9:648-652 (2002). "Hematopoietic, vascular and cardiac fates of bone marrow-derived stem cells."
Hofstetter et al., PNAS USA, 99:2199-2204. "Marrow stromal cells from guiding strands in the injured spinal cord and promote recovery."
Aoki et al., Stem Cells, 22:994-1002 (2004), "Derivation of Functional Endothelial Progenitor Cells from Human Umbilical Cord Blood Mononuclear Cells Isolated by a Novel Cell Filtration Device."
Bagley et al., Cancer Research, 63:5866-5873 (2003). "Endothelial Precursor Cells as a Model of Tumor Endothelium; Characterization and Comparison with Mature Endothelial Cells."
Bompais et al., Blood, 103(7):2577-2584 (2004). "Human endothelial cells derived from circulating progenitors display specific functional properties compared with mature vessel wall endothelial cells."
Finkenzeller et al., Cell Prolif., 42:498-505 (2009). "Impaired in vivo vasculogenic potential of endothelial progenitor cells in comparison to human umbilical vein endothelial cells in a spheroid-based implantation model."
Graham, The Scientific World Journal, 2:1540-1543 (2002). "Separation of Monocytes from Whole Human Blood."
Hu et al., Proc. Natl. Acad. Sci., 88:2227-2231 (1991), "An angiogenin-binding protein from endothelial cells."
Ingram et al., Blood, 105(7):2783-2786 (2005). "Vessel wall-derived endothelial cells rapidly proliferate because they contain a complete hierarchy of endothelial progenitor cells."
An Office Action dated Jan. 22, 2013, which issued during the prosecution of U.S. Appl. No. 11/820,975.
An Office Action dated Nov. 6, 2012, which issued during the prosecution of U.S. Appl. No. 12/224,913.
An Office Action dated Apr. 19, 2013, which issued during the prosecution of Canadian Patent Application No. 2,632,834.
An Office Action dated Oct. 18, 2012, which issued during the prosecution of Canadian Patent Application No. 2,632,836.
Response filed on Jan. 31, 2013 during the prosecution of U.S. Appl. No. 12/224,913 including exhibits A-D.
An Office Action dated Sep. 26, 2013, which issued during the prosecution of European Patent Application No. 07 713 328.8.
De Almeida M C et al:"A simple method for Human Peripheral Blood Monocyte Isolation", Memorias Do Instituto Oswaldo Cruz, Rio De Janeiro, BR, vol. 95, No. 2,Jan. 1, 2000, pp. 221-223, XP003023526.
An Office Action dated Nov. 4, 2013, which issued during the prosecution of Canadian Patent Application No. 2,632,836.
An Office Action dated Jul. 26, 2013, which issued during the prosecution of European Patent Application No. 10190450.6.
An International Preliminary Report on Patentability dated Mar. 10, 2009, which issued during the prosecution of Applicant's PCT/IL2007/000308.
An Office Action dated Jul. 31, 2013, which issued during the prosecution of Canadian Patent Application No. 2,645,142.
An English Translation of an Office Acton dated Jul. 26, 2012 which issued during the prosecution of Korean Patent Application No. 10-2007-7000060.
An Office Action dated Feb. 8, 2012, which issued during the prosecution of Canadian Patent Application No. 2,567,578.

* cited by examiner

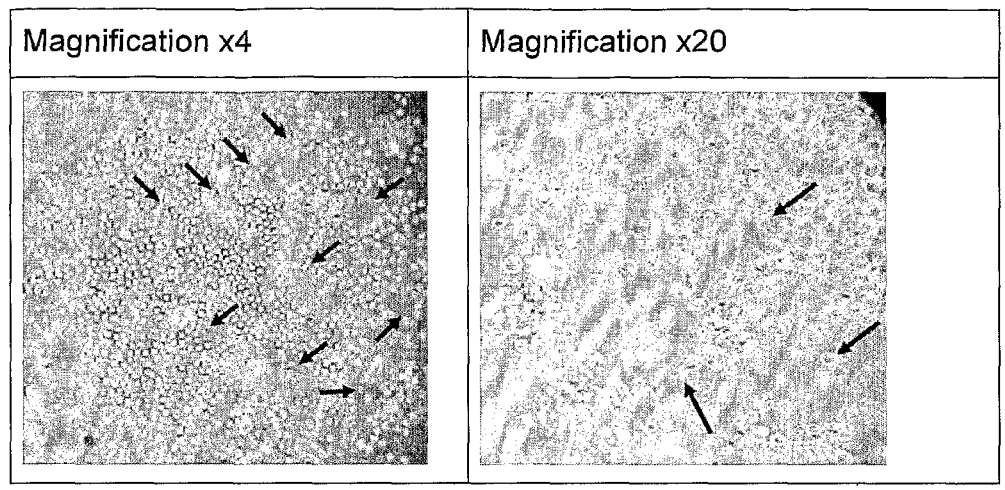

IN VITRO TECHNIQUES FOR USE WITH STEM CELLS

CROSS-REFERENCES TO RELATED APPLICATIONS

This application is a §371 national stage entry of PCT International Application No. PCT/IL2005/000571 filed Jun. 1, 2005, which claims benefit of U.S. Provisional Application No. 60/588,520, filed Jul. 15, 2004, and U.S. Provisional Application No. 60/576,266, filed Jun. 1, 2004, the contents of all of which are incorporated by reference into this application.

FIELD OF THE INVENTION

The present invention relates generally to methods and apparatus for treatment of human patients suffering from vascular disorders, and specifically to methods and apparatus for facilitating angiogenesis and/or neovascularization and/or vasculogenesis.

BACKGROUND OF THE INVENTION

Some arterial dysfunction occurs due to narrowing of the arteries by fatty deposits or other vascular abnormalities. This may interfere with blood flow and/or prevent tissues and organs from being supplied with sufficient nutrients and oxygen.

Vascular disorders are common conditions and can severely compromise a patient's quality of life. Despite considerable advances in medical therapy and improvements in revascularization procedures for artery dysfunction, such as coronary artery graft, balloon angioplasty and stenting of the coronary vessels, a substantial proportion of patients suffer from artery dysfunction-derived disease.

Endothelial progenitor cells (EPCs) have been used to treat patients suffering from vascular diseases. In such severe cases, when drugs or direct revascularization procedures are not effective anymore, or cannot be used, alternative therapies are required. EPCs have been applied to ischemic tissue. EPCs have the ability to differentiate in order to form endothelium, the layer of cells forming blood vessels. These cells are involved in re-endothelialization, neovascularization, vasculogenesis and angiogenesis processes. The mechanisms by which implanted EPCs can become part of the healing process include self-repopulation, fusion with cells of the injured tissue and secretion of cytokines and growth factors. Repopulation of EPCs and their differentiation into mature endothelial cells enables their functions in re-endothelialization, neovascularization, vasculogenesis and angiogenesis processes. Recent evidence suggests that fusion of EPCs with cells of injured tissue enhances tissue function regeneration. Moreover, following secretion of cytokines and growth factors, EPCs can influence cellular survival of cells inherent to the tissue, and may help the mobilization of stem cells to the injured tissue.

A common ancestor cell, the hemangioblast, gives rise to both endothelial and hematopoietic (blood cell) precursors. This ancestor cell differentiates into hematopoietic stem cells and angioblasts, which are mesodermal precursor cells, differentiating into endothelial precursors. These cells have the capacity to proliferate, migrate, and differentiate into endothelial cells, but have not yet acquired specific mature endothelial markers. Following commitment to the endothelial lineage, angioblasts assemble into a primitive vascular plexus of veins and arteries, in a process called vasculogenesis. This primitive vasculature is subsequently refined into a functional network by angiogenesis and by remodeling and arteriogenesis of newly formed vessels. EPCs have been shown to mobilize (i.e., migrate in increased numbers from the bone marrow (BM) into the circulation) in patients with vascular trauma or Acute Myocardial Infarction (AMI) (See, for example, the following two articles which are incorporated herein by reference: (a) Gill, M., S. Dias, et al. (2001), "Vascular trauma induces rapid but transient mobilization of VEGFR2(+)AC133(+) endothelial precursor cells," Circ Res 88(2): 167-74; and (b) Shintani, S., T. Murohara, et al. (2001), "Mobilization of endothelial progenitor cells in patients with acute myocardial infarction," Circulation 103(23): 2776-9.) In general, the use of EPCs aims to promote the formation of natural bypasses within the ischemic or scarred tissue and thus alleviate the clinical condition of these patients.

Numerous animal experiments and clinical trials have investigated the potential of this therapy to augment blood flow and yield an associated alleviation of ischemic symptoms, as manifested by a patient's improvement in physical functioning.

Various sources for autologous EPCs for transplantation have been described, including stem cells aspirated directly from the bone marrow (BM), and BM-derived peripheral blood stem cells.

Progenitor cells, or stem cells, include bone marrow cells that can multiply, migrate and differentiate into a wide variety of cell types. Bone marrow hematopoietic stem cells are characterized as being "CD34 positive" (CD34+), i.e., expressing the CD34 marker.

It is assumed that the plasticity of well-defined populations of hematopoietic progenitors allows them to trans-differentiate in response to the environmental cues present in the target organ, and, more specifically, to convert into endothelial cells.

Transplantation of bone marrow is clinically appealing because of the relative simplicity of the medical procedure. It entails aspiration of bone marrow from the iliac crest and immediate re-injection of the aspirate or selected cells into the post-infarction scar. Nevertheless, the procedure is invasive and must be done under anesthesia.

The first evidence indicating the presence of EPCs in the adult circulation was obtained when mononuclear blood cells from healthy human volunteers were shown to acquire an endothelial cell-like phenotype in vitro and to incorporate into capillaries in vivo. (See Asahara, T., T. Murohara, et al. (1997), "Isolation of putative progenitor endothelial cells for angiogenesis," Science 275(5302): 964-7, which is incorporated herein by reference.) These putative EPCs were characterized via expression of CD34 and vascular endothelial growth factor receptor-2 (VEGFR-2/KDR), two antigens shared by embryonic endothelial progenitors, and hematopoietic stem cells (HSCs). In addition to CD34, early hematopoietic progenitor cells express CD133 (AC133), which is not expressed after differentiation. Currently, the widely accepted definition of EPCs in circulation is, for practical purposes, CD34+/VEGFR-2+ or CD133+/VEGFR-2+ cells.

Peripheral blood EPCs can be obtained from blood of untreated patients or from patients treated in order to augment EPC mobilization using cytokines such as granulocyte-colony stimulating factor (G-CSF), granulocyte monocyte colony-stimulating factor (GM-CSF), vascular endothelial growth factor (VEGF), and fibroblast growth factor (FGF). The mobilization treatments are typically avoided in patients who suffer from hematological and arterial derived disorders. Treatments such as HMG CoA reductase inhibitors (statins) have also been reported to elevate numbers of EPCs in circulation. See, for example:

1. Dimmeler S., et al. (2001), "HMG-CoA reductase inhibitors (statins) increase endothelial progenitor cells via the PI 3-kinase/Akt pathway," J. Clin. Invest. 108: 391-397.
2. Hyun-Jae, Hyo-Soo Kim, et al. (2003), "Effects of intracoronary infusion of peripheral blood stem-cells mobilized with granulocyte-colony stimulating factor on left ventricular systolic function and restenosis after coronary stenting in myocardial infraction: the MAGIC cell randomized clinical trial," The Lancet 363: 751-756.
3. Brigit Assmus, Volker Schachinger et al., (2002), "Transplantation of progenitor cells and regeneration enhancement in acute myocardial infraction (TOPCARE-AMI)," Circulation 106: 3009-3017.
4. Alexandra Aicher, Winfreid Brenner, et al., (2003), "Assessment of the tissue distribution of transplanted human endothelial progenitor cells by radioactive labeling," Circulation 107: 2134-2139.

Each of these articles is incorporated herein by reference.

The procedure for removing peripheral blood is simpler and more convenient for the patient than BM removal. The fact that EPCs can be isolated from peripheral blood is an additional important factor in the choice of using these cells for therapy. The isolation of progenitor cells from BM, which contains many more cell types, is technically more challenging, as well.

Results from EPC and BMC treatments show improved cardiac function, greater capillary density, marked increase in number of collateral vessels, improvement of echocardiographic left ventricular ejection fraction, decrease in ischemic area scarring and prevention of cardiomyocyte apoptosis in rat models of myocardial infarction. Furthermore, improved blood flow and capillary density and reduced rate of limb loss in hindlimb was shown in an ischemia model in nude mice.

The following articles, which are incorporated herein by reference, describe techniques which may be used in combination with techniques described herein:

(1) Kalka, C., H. Masuda, et al. (2000). "Vascular endothelial growth factor (165) gene transfer augments circulating endothelial progenitor cells in human subjects." Circ Res 86(12): 1198-202.

(2) Kawamoto, A., H. C. Gwon, et al. (2001). "Therapeutic potential of ex vivo expanded endothelial progenitor cells for myocardial ischemia." Circulation 103(5): 634-7.

(3) Kawamoto, A., T. Tkebuchava, et al. (2003). "Intramyocardial transplantation of autologous endothelial progenitor cells for therapeutic neovascularization of myocardial ischemia." Circulation 107(3): 461-8.

(4) Kamihata, H., H. Matsubara, et al. (2001). "Implantation of bone marrow mononuclear cells into ischemic myocardium enhances collateral perfusion and regional function via side supply of angioblasts, angiogenic ligands, and cytokines." Circulation 104(9): 1046-52.

(5) Kocher, A. A., M. D. Schuster, et al. (2001). "Neovascularization of ischemic myocardium by human bone-marrow-derived angioblasts prevents cardiomyocyte apoptosis, reduces remodeling and improves cardiac function." Nat Med 7(4): 430-6.

The following articles and book chapter, which are also incorporated herein by reference, describe techniques which may be used in combination with techniques described herein:

Flammera J et al. (2002). "The impact of ocular blood flow in glaucoma." Progress in Retinal and Eye Research 21:359-393.

Zarbin M A (2004). "Current concepts in the pathogenesis of age-related macular degeneration." Arch Opthalmol. 122(4):598-614.

Frank R N (2004). "Diabetic retinopathy." N Engl J Med 350:48-58.

Singleton J R (2003). "Microvascular complications of impaired glucose tolerance." Diabetes 52:2867-2873.

Bahlmann F H et. (2004). "Erythropoietin regulates endothelial progenitor cells." Blood 103(3):921-6.

Greenfield, Ed. (2001). "Surgery: scientific principles and practice." Lippincot: Philadelphia, chapter 107.

Kouwenhoven E A et al. (2000). "Etiology and pathophysiology of chronic transplant dysfunction." Transplant Internat. 13(6):385-401.

Browne E Z et al. (1986). "Complications of skin grafts and pedicle flaps." Hand Clin. 2:353-9.

Chen et al. (1991). "Four types of venous flaps for wound coverage: a clinical appraisal." J. Trauma 31(9):1286-93.

Beatrice et al. (2004) Dermatol. Surg. 30(3):399.

Ferretti et al. (2003). "Angiogenesis and nerve regeneration in a model of human skin equivalent transplant." Life Sci. 73:1985-94.

Schechner et al. (2003). "Engraftment of a vascularized human skin equivalent." FASEB J. 17(15):2250-60.

Research has been carried out in humans during the last few years to examine the potential benefits of using EPCs and other bone marrow derived cells to treat myocardial disorders. Recent studies demonstrate that implantation of autologous progenitor cells after Acute Myocardial Infarction appears to limit post-infarction damage. The following clinical trials focus on the studies that assessed the safety and efficacy of bone marrow-derived or blood-derived cells administered in patients with cardiac disorders.

Perin et al. carried out a clinical trial which included 21 patients (14 in the treatment group, 7 in the control group) who received transendocardial injections of autologous mononuclear BMCs. (See Perin, E. C., H. F. Dohmann, et al. (2003), "Transendocardial, autologous bone marrow cell transplantation for severe, chronic ischemic heart failure," Circulation 107(18): 2294-302, which is incorporated herein by reference.) At 4 months, there was an improvement in ejection fraction, a reduction in end-systolic volume, and significant mechanical improvement of the injected segments in the treated patients.

Another group injected autologous EPCs into the infarct border zone in six patients who had suffered from myocardial infarction and undergone coronary artery bypass grafting. Three to nine months after surgery, all patients were alive and well, and global left-ventricular function was enhanced in four patients. All six patients reported a notable improvement in exercise capacity. Myocardial perfusion scans were reported to have improved strikingly by qualitative analysis in five of six patients. The results of this study indicate that implantation of EPCs to the heart probably induces angiogenesis, thus improving perfusion of the infarcted myocardium. (See Stamm, C., B. Westphal, et al. (2003), "Autologous bone-marrow stem-cell transplantation for myocardial regeneration," Lancet 361(9351): 45-6, which is incorporated herein by reference.)

The Transplantation of Progenitor Cells and Regeneration Enhancement in Acute Myocardial Infarction (TOPCARE-AMI) study involved the delivery of circulating endothelial progenitor cells or bone marrow cells directly into coronary arteries after the infarction in patients with reperfused acute myocardial infarction (See Assmus, B., V. 15, Schachinger, et al. (2002), "Transplantation of Progenitor Cells and Regeneration Enhancement in Acute Myocardial Infarction (TOP-CARE-AMI)," Circulation 106(24): 3009-17, which is incorporated herein by reference.) In the first 20 patients, 11 received EPCs and 9 received BMCs. At 4 months, transplantation of progenitor cells resulted in a significant increase in global left ventricular ejection fraction, echocardiography revealed improved regional wall motion in the infarct zone, reduced end-systolic left ventricular volumes, and increased myocardial viability in the infarct zone compared with a nonrandomized, matched reference group. There were no adverse events of treatment in any of the patients such arrhythmias, or increase in creatine kinase and troponin. There was no difference between BM- and peripheral blood-derived cells.

A study performed by a team led by Amit Patel of University of Pittsburgh, involved 20 patients with severe heart failure out of which 10 were injected into the coronary vessels with BM derived EPCs. At one-, three- and six-month follow-up, the ejection fraction rates for the stem cell patients were significantly improved compared to the other patients. (See Abstract from American Association for Thoracic Surgery, Toronto, May 2004).

The following articles, which are incorporated herein by reference, may also be of interest:

- J. Folkman, Y. Shing, J. Biol. Chem. 267, 10931 (1992)
- W. Brugger, S. Heimfeld, R. J. Berenson, R. Mertelsmann, L. Kanz, N. Engl J. Med. 333, 283 (1995)
- F. Katz, R. W. Tindle, D. R. Sutherland, M. D. Greaves, Leuk. Res. 9, 191 (1985)
- R. G. Andrews, J. W. Singer, I. D. Bernstein, Blood 67, 842 (1986)
- B. I. Terman, M. Dougher-Vermazen, M. E. Carrion, D. Dimitrov, D. C. Armellino, et al, Biochem. Biophys. Res. Commun. 187, 1579 (1992)
- B. Millauer, S. Wizigmann-Voos, H. Schnurch, R. Martinez, N. P. H. Moller, et al, Cell 72, 835 (1993)
- J. C. Voyta, D. P. Via, C. E. Butterfield, B. R. Zetter, J. Cell Biol. 99, 2034 (1984)
- P. J. Newman, M. C. Berndt, J. Gorski, G. C. White, S. Lyman, et al, Science 247, 1219 (1990)
- T. N. Sato, Y. Tozawa, U. Deutsch, K. Wolburg-Buchholz, Y. Fujiwara, et al, Nature 376, 70 (1995)
- H. Schnurch, W. Risau, Development 119, 957 (1993)
- J. L. Liesveld, K. E. Frediani, A. W. Harbol, J. F. DiPersio, C. N. Abboud, Leukemia 8, 2111 (1994).
- S. Takeshita, L. P. Zheng, E. Brogi, M. Kearney, L. Q. Pu, et al, J. Clin. Invest. 93, 662 (1994)
- R. Baffour, J. Berman, J. L. Garb, S. W. Rhee, J. Kaufman, et al, J. Vasc. Surg. 16, 181 (1992)
- J. M. Isner, A. Pieczek, R. Schainfeld, R. Blair, L. Haley, et al, Lancet 348, 370 (1996)
- Y. Sato, K. Okamura, A. Morimoto, R. Hamanaka, K. Hamanaguchi, et al, Exp. Cell Res. 204, 223 (1993)

The following articles, which are also incorporated herein by reference, may also be of interest:

- Badorff, C., R. P. Brandes, et al. (2003). "Transdifferentiation of blood-derived human adult endothelial progenitor cells into functionally active cardiomyocytes." Circulation 107(7): 1024-32.
- Bhattacharya, V., P. A. McSweeney, et al. (2000). "Enhanced endothelialization and microvessel formation in polyester grafts seeded with CD34(+) bone marrow cells." Blood 95(2): 581-5.
- Grant, M. B., W. S. May, et al. (2002). "Adult hematopoietic stem cells provide functional hemangioblast activity during retinal neovascularization." Nat Med 8(6): 607-12.
- Hirata, K., T. S. Li, et al. (2003). "Autologous bone marrow cell implantation as therapeutic angiogenesis for ischemic hindlimb in diabetic rat model." Am J Physiol Heart Circ Physiol 284(1): H66-70.
- Ikenaga, S., K. Hamano, et al. (2001). "Autologous bone marrow implantation induced angiogenesis and improved deteriorated exercise capacity in a rat ischemic hindlimb model." J Surg Res 96(2): 277-83.
- Kalka, C., H. Masuda, et al. (2000). "Transplantation of ex vivo expanded endothelial progenitor cells for therapeutic neovascularization." Proc Natl Acad Sci USA 97(7): 3422-7.
- Kaushal, S., G. E. Amiel, et al. (2001). "Functional small-diameter neovessels created using endothelial progenitor cells expanded ex vivo." Nat Med 7(9): 1035-40.
- Kornowski, R., M. B. Leon, et al. (2000). "Electromagnetic guidance for catheter-based transendocardial injection: a platform for intramyocardial angiogenesis therapy. Results in normal and ischemic porcine models." J Am Coll Cardiol 35(4): 1031-9.
- Li, R. K., Z. Q. Jia, et al. (1996). "Cardiomyocyte transplantation improves heart function." Ann Thorac Surg 62(3): 654-60; discussion 660-1.
- Rajnoch, C., J. C. Chachques, et al. (2001). "Cellular therapy reverses myocardial dysfunction." J Thorac Cardiovasc Surg 121(5): 871-8.
- Schatteman, G. C., H. D. Hanlon, et al. (2000). "Blood-derived angioblasts accelerate blood-flow restoration in diabetic mice." J Clin Invest 106(4): 571-8.
- Shintani, S., T. Murohara, et al. (2001). "Augmentation of postnatal neovascularization with autologous bone marrow transplantation." Circulation 103(6): 897-903.
- Strauer, B. E., M. Brehm, et al. (2002). "Repair of infarcted myocardium by autologous intracoronary mononuclear bone marrow cell transplantation in humans." Circulation 106(15): 1913-8.
- Taylor, D. A., B. Z. Atkins, et al. (1998). "Regenerating functional myocardium: improved performance after skeletal myoblast transplantation." Nat Med 4(8): 929-33.
- Thompson, C. A., B. A. Nasseri, et al. (2003). "Percutaneous transvenous cellular cardiomyoplasty. A novel non-surgical approach for myocardial cell transplantation." J Am Coll Cardiol 41(11): 1964-71.
- Tomita, S., R. K. Li, et al. (1999). "Autologous transplantation of bone marrow cells improves damaged heart function." Circulation 100(19 Suppl): 11247-56.
- Tomita, S., D. A. Mickle, et al. (2002). "Improved heart function with myogenesis and angiogenesis after autologous porcine bone marrow stromal cell transplantation." J Thorac Cardiovasc Surg 123(6): 1132-40.
- Wang et al. (2004). "Rosiglitazone facilitates angiogenic progenitor cell differentiation toward endothelial lineage: a new paradigm in glitazone pleiotropy." Circulation 109(11): 1392-400.
- Rupp et al. (2004). "Statin therapy in patients with coronary artery disease improves the impaired endothelial progenitor cell differentiation into cardiomyogenic cells." Basic Res Cardiol. 99(1): 61-8.
- Quirici et al. (2001). "Differentiation and expansion of endothelial cells from human bone marrow CD133(+) cells." Br J. Haematol. 115(1): 186-94.
- Di Stefano et al. (2002) "Different growth conditions for peripheral blood endothelial progenitors." Cardiovasc Radiat Med. 3(3-4): 172-5.

Akita et al. (2003). "Hypoxic preconditioning augments efficacy of human endothelial progenitor cells for therapeutic neovascularization." Lab Invest. 83(1): 65-73.

Wang et al. (2004). "Mechanical, cellular, and molecular factors interact to modulate circulating endothelial cell progenitors." Am J Physiol Heart Circ Physiol. 286(5): H1985-93.

Bahlmann et al. (2003). "Endothelial progenitor cell proliferation and differentiation is regulated by erythropoietin." Kidney Int. 64(5): 1648-52.

Heeschen et al. (2003). "Erythropoietin is a potent physiologic stimulus for endothelial progenitor cell mobilization." Blood. 102(4): 1340-6.

Verma et al. (2004). "C-reactive protein attenuates endothelial progenitor cell survival, differentiation, and function: Further evidence of a mechanistic link between C-reactive protein and cardiovascular disease." Circulation. 109(17): 2058-67.

U.S. Pat. Nos. 5,980,887, 6,569,428, and 6,676,937 to Isner et al., which are incorporated herein by reference, generally describe pharmaceutical products including EC progenitors for use in methods for regulating angiogenesis, i.e., for enhancing or inhibiting blood vessel formation, in a selected patient and in some preferred embodiments for targeting an angiogenesis modulator to specific locations. For example, the EC progenitors can be used to enhance angiogenesis or to deliver an angiogenesis modulator, e.g., anti- or pro-angiogenic agents, respectively to sites of pathologic or utilitarian angiogenesis. Additionally, in another embodiment, EC progenitors can be used to induce re-endothelialization of an injured blood vessel, and thus reduce restenosis by indirectly inhibiting smooth muscle cell proliferation.

U.S. Pat. No. 5,541,103 to Kanz et al., which is incorporated herein by reference, describes high-dose chemotherapy treatments for patients suffering from certain types of cancer. In order to facilitate recovery, a process for the ex vivo expansion of peripheral blood progenitor cells is described, wherein CD34+ cells are enriched and cultivated in a medium comprising IL-1, IL-3, IL-6, EPO and SCF. The ex vivo expanded peripheral blood progenitor cells can be administered to cancer patients after chemotherapy.

US Patent Application Publication 2003/0199464 to Itescu, which is incorporated herein by reference, describes a method for treating a disorder of a subject's heart involving loss of cardiomyocytes. The method includes administering to the subject an amount of an agent described as being effective to cause cardiomyocyte proliferation within the subject's heart so as to thereby treat the disorder. In an embodiment, the agent is human endothelial progenitor cells. The application also describes methods for determining the susceptibility of a cardiomyocyte in a subject to apoptosis.

PCT Patent Publication WO 01/94420 to Itescu, which is incorporated herein by reference, describes a method of stimulating vasculogenesis of myocardial infarct damaged tissue in a subject comprising: (a) removing stem cells from a location in the subject; (b) recovering endothelial progenitor cells from the stem cells; (c) introducing the endothelial progenitor cells from step (b) into a different location in the subject such that the precursors migrate to and stimulate revascularization of the tissue. The stem cells may be removed directly or by mobilization. The endothelial progenitor cells may be expanded before introduction into the subject. A method of inducing angiogenesis in peri-infarct tissue is described. A method is also described for selectively increasing the trafficking of human bone marrow-derived endothelial cell precursors to the site of tissue damaged by ischemic injury, which comprises: (a) administering endothelial progenitor cells to a subject; (b) administering chemokines to the subject so as to thereby attract endothelial cell precursors to the ischemic tissue. A method is also described for stimulating vasculogenesis or angiogenesis of myocardial infarct damaged tissue in a subject comprising injecting allogeneic stem cells into a subject. A method is also described for improving myocardial function in a subject that has suffered a myocardial infarct comprising any of the instant methods. A method is also described for improving myocardial function in a subject who has suffered a myocardial infarct comprising injecting G-CSF or anti-CXCR4 antibody into the subject in order to mobilize endothelial progenitor cells.

U.S. Pat. No. 5,199,942 to Gillis, describes a method for autologous hematopoietic cell transplantation of patients receiving cytoreductive therapy, including: (1) obtaining hematopoietic progenitor cells from bone marrow or peripheral blood from a patient prior to cytoreductive therapy; (2) expanding the hematopoietic progenitor cells ex vivo with an ex vivo growth factor selected from the group consisting of interleukin-3 (IL-3), steel factor (SF), granulocyte macrophage-colony stimulating factor (GM-CSF), interleukin-1 (IL-1), GM-CSF/IL-3 fusion proteins and combinations thereof, to provide a cellular preparation comprising an expanded population of progenitor cells; and (3) administering the cellular preparation to the patient concurrently with or following cytoreductive therapy. The method optionally includes a preliminary treatment with a recruitment growth factor to recruit hematopoietic progenitor cells into peripheral blood and a subsequent treatment with an engraftment growth factor to facilitate engraftment and proliferation of hematopoietic progenitor cells administered in the cellular preparation. The patent also describes a hematopoietic progenitor cell expansion media composition comprising cell media, an ex vivo growth factor, and autologous serum.

U.S. Pat. No. 4,656,130 to Shoshan, which is incorporated herein by reference, describes a collagen coated cell growth plate that includes a substrate coated with a storage stable coating of collagen fibrils. The method of preparing the collagen coated cell growth plates comprises dispensing biologically active collagen fibrils suspended in distilled water onto a tissue culture dish. Thereafter, the dish containing the collagen fibril suspension is placed in a laminar flow hood provided with a sterile air stream and ultraviolet light. The fibrils sediment and adhere to the bottom of the dish, the water evaporates in the sterile air stream and is removed in the laminar flow hood exhaust, and the ultraviolet light ensures that the resulting thin layer of collagen fibrils is sterile and ready for the inoculation of living cells. The method is described as yielding a convenient precoated cell growth plate which can maintain reasonable shelf life when kept at room temperature without any significant decrease in cell growth support properties.

U.S. Pat. No. 5,932,473 to Swiderek et al., which is incorporated herein by reference, describes a cell culture substrate that is coated with a composition containing a cell adhesion promoter in a salt solution. A substrate such as plastic, glass or microporous fibers is coated with a composition containing about 5-1000 ug/ml of poly-D-lysine in an 0.005-0.5 M citrate or sulfate salt solution, in order to provide about 50-500 ul of the composition per cm2 of substrate. The coated substrate is rinsed to remove extraneous materials, and dried to obtain a coated substrate having increased shelf-life and/or stability. The coated substrate may be sterilized by rinsing with a sterilizing medium such as ethanol.

U.S. Pat. No. 6,040,182 to Septak, which is incorporated herein by reference, describes methods and materials for the facilitation of high-protein-binding capability on tissue culture-treated plastic surfaces, such as, for example, polystyrene assay plates.

U.S. Pat. No. 4,450,231 to Ozkan, which is incorporated herein by reference, describes an immunoassay of a specimen of a serum or the like to determine immune complexes. A method is described which includes producing on a plastic base a layer of a non-proteinaceous, non-ionic polymer which will adhere to the plastic base and has the capability of absorbing immune complexes of the specimen, placing a specimen on the layer and treating the layer to produce an indication of the amount of immune complexes. The polymer may be polyethylene glycol, dextran, polyvinyl chloride, a polymeric polyol or an adduct of polyethylene glycol. A product for use in such an assay is a plate having wells or a test tube formed of plastic, polystyrene and polyvinyl chloride being preferred, with a layer of such non-proteinaceous, non-ionic layer on the plate wells or the cavity of the test tube.

US Patent Application Publication 2003/0229393 to Kutryk et al., which is incorporated herein by reference, describes compositions and methods for producing a medical device such as a stent, a stent graft, a synthetic vascular graft, or heart valves, which are coated with a biocompatible matrix which incorporates antibodies, antibody fragments, or small molecules, which recognize, bind to and/or interact with a progenitor cell surface antigen to immobilize the cells at the surface of the device. The coating on the device can also contain a compound or growth factor for promoting the progenitor endothelial cell to accelerate adherence, growth and differentiation of the bound cells into mature and functional endothelial cells on the surface of the device to prevent intimal hyperplasia. Methods for preparing such medical devices, compositions, and methods for treating a mammal with vascular disease such as restenosis, atherosclerosis or other types of vessel obstructions are described.

SUMMARY OF THE INVENTION

The present patent application details methods for isolation, differentiation and expansion of stem cells from a tissue. For example, the stem cells may include endothelial progenitor cells (EPCs). Alternatively or additionally, the tissue may include human peripheral blood. Typically, the stem cells are transplanted into the donor or into another individual (e.g., in order to enhance vasculogenesis and/or angiogenesis and/or neovascularization). The present patent application provides protocols for obtaining a product containing appropriate numbers of functional EPCs. The methods described include: (a) Extraction of cellular sub-populations from a tissue; (b) expansion and differentiation of EPCs in culture for 1-30 days (or 3-30 or 4, 5, 6, 7, or 8 days) in enriched culture medium; and/or (c) identification of cellular components of the culture; (d) implantation of appropriate number of EPCs into a patient. It is to be understood that whereas some embodiments described herein relate specifically to EPCs derived from blood, the scope of the present invention includes techniques for use with stem cells derived from a variety of body tissues, mutatis mutandis.

For some applications, the method comprises collecting a blood sample from a donor and/or a patient, isolating from the sample peripheral blood mononuclear cells, separating a population of cells rich in CD31, and progenitor cells from the mononuclear cell fraction, and growing these cells under conditions that will cause the hematopoietic progenitor cells present in the mixture of cells to differentiate into EPCs and proliferate. This ex vivo expansion step is typically utilized because the number of EPCs in the circulation is below 0.1%.

Following this augmentation stage, the cells may be implanted by injection into blood vessels in the target organ, such as the coronary vessels or into the myocardium of a patient.

There is therefore provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and increasing the number of cells having a density between 1.055 and 1.068 g/ml, by culturing the second-pass cells for a period lasting between 3 and 30 days.

In an embodiment, applying the blood cells to the first gradient includes applying the blood cells to a gradient including copolymers of sucrose and epichlorohydrin such as FICOLL PAQUE PLUS™. (Amersham Biosciences, Uppsala, Sweden) or LYMPHOPREP™ (Axis-Shield PoC AS, Oslo, Norway) or obtainable from another source. In an embodiment, the density gradient is prepared by a technician on site.

In an embodiment, applying the first-pass cells to the second gradient includes applying the first-pass cells to a gradient, including an aqueous solution of Iodixanol such as OptiPrep™ or Nycodenz™ (Axis-Shield PoC AS, Oslo, Norway).

In an embodiment, applying the first-pass cells to the second gradient includes applying the first-pass cells to a gradient, including polyvinylpyrrolidone-coated silica colloids such as PERCOLL™ (Amersham Biosciences, Uppsala, Sweden).

There is further provided, in accordance with an embodiment of the present invention, a method for use with extracted stem cells, including:

applying tissue including the stem cells to a first gradient suitable for selecting first-pass cells having a density less than 1.077 g/ml;

applying the first-pass cells to a second gradient suitable for selecting second-pass cells having a density between 1.055 and 1.074 g/ml;

applying the second-pass cells to a third gradient suitable for selecting third-pass cells having a density between 1.055 and 1.068 g/ml; and increasing the number of cells having a density between 1.055 and 1.068 g/ml, by culturing the third-pass cells for a period lasting between 3 and 30 days.

In an embodiment, the third gradient is suitable for selecting cells having a density between 1.059 and 1.068 g/ml, and wherein applying the second-pass cells to the third gradient includes selecting the cells having a density between 1.059 and 1.068 g/ml.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and incubating the second-pass cells on a surface including (e.g., coated with) plasma and/or an antibody.

There is additionally provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and incubating the second-pass cells on a surface including a growth-enhancing molecule other than collagen or fibronectin.

In an embodiment, incubating the second-pass cells includes incubating the second-pass cells on a surface that includes, in addition to the growth-enhancing molecule, at least one of: collagen and fibronectin.

There is yet additionally provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells for a period lasting between 1 and 5 days in a culture medium including up to 5% serum (e.g., no serum, less than 1% serum, or between 1 and 5% serum).

There is still additionally provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells for a period lasting between 1 and 5 days in a culture medium including greater than or equal to 10% serum.

In an embodiment, culturing the second-pass cells includes culturing the second-pass cells in a culture medium including less than 20% serum.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a low-serum time period, culturing the second-pass cells in a culture medium including less than 10% serum; and during a high-serum time period, culturing the second-pass cells in a culture medium including greater than 10% serum.

In an embodiment, culturing the second-pass cells during the low-serum time period includes culturing the second-pass cells for a duration of between 1 and 5 days.

In an embodiment, culturing the second-pass cells during the high-serum time period includes culturing the second-pass cells for a duration of between 1 and 30 days.

In an embodiment, culturing the second-pass cells during the low-serum time period is performed prior to culturing the second-pass cells during the high-serum time period.

In an embodiment, culturing the second-pass cells during the low-serum time period is performed following culturing the second-pass cells during the high-serum time period.

There is further provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a hypoxic and/or hypercapnic (H/H) time period lasting at least 2 hours, culturing the second-pass cells under H/H conditions; and during a non-H/H time period lasting at least 1 day, culturing the second-pass cells under non-H/H conditions.

In the context of the present patent application and in the claims, the term hypercapnia refers to a concentration of $CO_2$ that is greater than 5%.

In an embodiment, the H/H and non-H/H time-periods are within a culturing time period lasting less than 30 days, and culturing the second-pass cells under H/H conditions includes culturing the second-pass cells under H/H conditions during a first two days of the culturing time period.

In an embodiment, the H/H and non-H/H time-periods are within a culturing time period lasting less than 30 days, and culturing the second-pass cells under H/H conditions includes culturing the second-pass cells under H/H conditions during a last two days of the culturing time period.

In an embodiment, the H/H and non-H/H time-periods are within a culturing time period lasting less than 30 days, and culturing the second-pass cells under H/H conditions includes culturing the second-pass cells under H/H conditions for at least 2 hours between a first two days and a last two days of the culturing time period.

In an embodiment, culturing the second-pass cells under H/H conditions is performed prior to culturing the second-pass cells under non-H/H conditions.

In an embodiment, culturing the second-pass cells under H/H conditions is performed following culturing the second-pass cells under non-H/H conditions.

There is still further provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells in a culture medium including at least one of the following: erythropoietin, VEGF, IGF, FGF, a molecule from the estrogen family (e.g., 17-β-estradiol, estrone, estriol, an estradiol derivative, estradiol valerate, estradiol cypionate, mestranol, quinestrol), a molecule from the progestin-family (e.g., progesterone, hydroxyprogesterone caroate, medroxyprogesterone acetate), a statin (e.g. Simvastatin, Atorvastatin), and an antidiabetic agent (e.g., Rosiglitazone).

In an embodiment, the antidiabetic agent includes Rosiglitazone, and culturing the second-pass cells includes culturing the second-pass cells in a culture medium including Rosiglitazone.

In an embodiment, the statin includes Simvastatin or Atorvastatin, and culturing the second-pass cells includes culturing the second-pass cells in a culture medium including Simvastatin or Atorvastatin.

In an embodiment, hormone molecules from the estrogen and progestin families include 17-β-estradiol and progesterone, and culturing the second-pass cells includes culturing the second-pass cells in a culture medium including 17-β-estradiol and/or progesterone.

In an embodiment, hormone molecules from the estrogen and progestin families include 17-β-estradiol and progesterone, and culturing the second-pass cells includes culturing the second-pass cells in a culture medium including 17-β-estradiol and to which progesterone is added after a certain period.

In an embodiment, hormone molecules from the estrogen and progestin families include 17-β-estradiol and progesterone, and culturing the second-pass cells includes culturing the second-pass cells in a culture medium including progesterone and to which 17-β-estradiol is added after a certain period.

There is yet further provided, in accordance with an embodiment of the present invention, a method for use with extracted stem cells, including:

applying tissue including the stem cells to a first gradient suitable for selecting first-pass cells having a density less than 1.077 g/ml;

applying the first-pass cells to a second gradient suitable for selecting second-pass cells having a density between 1.055 and 1.074 g/ml; and increasing the number of cells having a density between 1.059 and 1.068 g/ml, by culturing the second-pass cells for a period lasting between 3 and 30 days.

In an embodiment, the method includes extracting the stem cells from bone marrow.

In an embodiment, the method includes mobilizing the stem cells from bone marrow to facilitate extraction of the stem cells.

In an embodiment, the method includes extracting the stem cells from blood, umbilical cord blood, an embryo, a fetus or a placenta.

In an embodiment, culturing the second-pass cells includes:

culturing the second-pass cells in a first container during a first portion of the period;

removing at least some of the second-pass cells from the first container at the end of the first portion of the period; and culturing, in a second container during a second portion of the period, the cells removed from the first container.

In an embodiment, removing the at least some of the second-pass cells includes selecting for removal cells that adhere to a surface of the first container.

In an embodiment, removing the at least some of the second-pass cells includes selecting for removal cells that do not adhere to a surface of the first container.

In an embodiment, the first container includes on a surface thereof a growth-enhancing molecule, and culturing the cells in the first container includes culturing the cells in the first container that includes the growth-enhancing molecule.

In an embodiment, the second container includes on a surface thereof a growth-enhancing molecule, and culturing the cells in the second container includes culturing the cells in the second container that includes the growth-enhancing molecule.

In an embodiment, the growth-enhancing molecule is selected from the list consisting of: plasma (which can be autologous, allogeneic or xenogeneic), collagen, fibronectin, a growth factor, and an antibody to a stem cell surface receptor.

There is therefore provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

increasing the number of cells having a density between 1.055 and 1.074 g/ml, by culturing the second-pass cells for a period lasting between 3 and 30 days; and identifying endothelial progenitor cells in the cultured cells.

In an embodiment, applying the blood to the first gradient includes applying the blood to a solution including a copolymer of sucrose and epichlorohydrin.

In an embodiment, applying the first-pass cells to the second gradient includes applying the first-pass cells to an aqueous solution of iodixanol.

In an embodiment, applying the first-pass cells to the second gradient includes applying the first-pass cells to a gradual density solution including polyvinylpyrrolidone-coated silica colloids.

In an embodiment, applying the blood cells to the first gradient includes applying the blood cells to a FICOLL like gradient.

In an embodiment, applying the first-pass cells to the second gradient includes applying the first-pass cells to an OPTIPREP like gradient.

In an embodiment, applying the first-pass cells to the second gradient includes applying the first-pass cells to a PERCOLL like gradient.

There is also provided, in accordance with an embodiment of the present invention, a method for use with extracted stem cells, including:

applying tissue including the stem cells to a first gradient suitable for selecting first-pass cells having a density less than 1.077 g/ml;

applying the first-pass cells to a second gradient suitable for selecting second-pass cells having a density between 1.055 and 1.074 g/ml;

applying the second-pass cells to a third gradient suitable for selecting third-pass cells having a density between 1.055 and 1.068 g/ml;

increasing the number of cells having a density between 1.055 and 1.068 g/ml, by culturing the third-pass cells for a period lasting between 3 and 30 days; and identifying endothelial progenitor cells in the cultured cells.

In an embodiment, the third gradient is suitable for selecting cells having a density between 1.059 and 1.068 g/ml, and wherein applying the second-pass cells to the third gradient includes selecting the cells having a density between 1.059 and 1.068 g/ml.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

culturing the second-pass cells on a surface including plasma; and identifying progenitor cells in the cultured cells.

In an embodiment, culturing includes culturing the second-pass cells on the surface, when the surface is coated with autologous plasma.

In an embodiment, culturing includes culturing the second-pass cells on the surface, when the surface is coated with at least one plasma selected from the list consisting of: allogeneic plasma and xenogeneic plasma.

There is also provided, in accordance with an embodiment of the present invention, a method for use with tissue, including:

culturing the tissue on a surface including plasma.

In an embodiment, the tissue includes blood.

In an embodiment, the plasma includes autologous plasma.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

culturing the second-pass cells on a surface including an antibody; and identifying progenitor cells in the cultured cells.

In an embodiment, the progenitor cells include endothelial progenitor cells (EPCs), and wherein identifying the progenitor cells includes identifying the EPCs.

In an embodiment, culturing includes culturing the second-pass cells on the surface, when the surface is coated with autologous plasma.

In an embodiment, culturing includes culturing the second-pass cells on the surface, when the surface is coated with at least one plasma selected from the list consisting of: allogeneic plasma and xenogeneic plasma.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

culturing the second-pass cells on a surface including a growth-enhancing molecule other than collagen or fibronectin; and identifying progenitor cells in the cultured cells.

In an embodiment, the progenitor cells include endothelial progenitor cells (EPCs), and wherein identifying the progenitor cells includes identifying the EPCs.

In an embodiment, culturing the second-pass cells includes culturing the second-pass cells on a surface that includes, in addition to the growth-enhancing molecule, at least one of: collagen and fibronectin.

There is also provided, in accordance with an embodiment of the present invention, method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

culturing the second-pass cells for a period lasting between 1 and 5 days in a culture medium including up to 5% serum; and identifying progenitor cells in the cultured cells.

In an embodiment, the progenitor cells include endothelial progenitor cells (EPCs), and wherein identifying the progenitor cells includes identifying the EPCs.

There is also provided, in accordance with an embodiment of the present invention, method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

culturing the second-pass cells for a period lasting between 1 and 5 days in a culture medium including greater than 10% serum; and identifying progenitor cells in the cultured cells.

In an embodiment, culturing the second-pass cells includes culturing the second-pass cells in a culture medium including less than 20% serum.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a low-serum time period, culturing the second-pass cells in a culture medium including less than 10% serum;

during a high-serum time period, culturing the second-pass cells in a culture medium including greater than or equal to 10% serum; and identifying progenitor cells in the cultured cells.

In an embodiment, culturing the second-pass cells during the low-serum time period includes culturing the second-pass cells in a culture medium including up to 5% serum.

In an embodiment, culturing the second-pass cells during the low-serum time period includes culturing the second-pass cells in a serum-free culture medium.

In an embodiment, culturing the second-pass cells during the low-serum time period includes culturing the second-pass cells for a duration of between 1 and 5 days.

In an embodiment, culturing the second-pass cells during the high-serum time period includes culturing the second-pass cells for a duration of between 1 and 30 days.

In an embodiment, culturing the second-pass cells during the low-serum time period is performed prior to culturing the second-pass cells during the high-serum time period.

In an embodiment, culturing the second-pass cells during the low-serum time period is performed following culturing the second-pass cells during the high-serum time period.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a hypoxic time period lasting at least 2 hours, culturing the second-pass cells under hypoxic conditions;

during a non-hypoxic time period lasting at least 1 day, culturing the second-pass cells under non-hypoxic conditions; and identifying progenitor cells in the cultured cells.

In an embodiment, the progenitor cells include endothelial progenitor cells (EPCs), and wherein identifying the progenitor cells includes identifying the EPCs.

In an embodiment, the hypoxic and non-hypoxic time-periods are within a culturing time period lasting less than 30 days, and wherein culturing the second-pass cells under hypoxic conditions includes culturing the second-pass cells under hypoxic conditions during a first two days of the culturing time period.

In an embodiment, the hypoxic and non-hypoxic time-periods are within a culturing time period lasting less than 30 days, and wherein culturing the second-pass cells under hypoxic conditions includes culturing the second-pass cells under hypoxic conditions during a last two days of the culturing time period.

In an embodiment, the hypoxic and non-hypoxic time-periods are within a culturing time period lasting less than 30 days, and wherein culturing the second-pass cells under hypoxic conditions includes culturing the second-pass cells under hypoxic conditions for at least 2 hours between a first two days and a last two days of the culturing time period.

In an embodiment, culturing the second-pass cells under hypoxic conditions is performed prior to culturing the second-pass cells under non-hypoxic conditions.

In an embodiment, culturing the second-pass cells under hypoxic conditions is performed following culturing the second-pass cells under non-hypoxic conditions.

There is also provided, in accordance with an embodiment of the present invention, a method for use with extracted blood, including:
applying blood to a gradient to select cells having a first desired density range;
increasing the number of cells having a second desired density range by culturing the selected cells in a medium including estrogen and subsequently in a medium including a progestin; and
identifying progenitor cells in the cultured cells.

There is also provided, in accordance with an embodiment of the present invention, method for use with extracted blood, including:
applying blood to a gradient to select cells having a first desired density range;
increasing the number of cells having a second desired density range by culturing the selected cells in a medium including a progestin and subsequently in a medium including estrogen; and
identifying progenitor cells in the cultured cells.

There is also provided, in accordance with an embodiment of the present invention, a method for use with extracted blood, including:
applying blood to a gradient to select cells having a first desired density range;
increasing the number of cells having a second desired density range by culturing the selected cells in a medium including estrogen and a progestin; and
identifying progenitor cells in the cultured cells.

In an embodiment, the progestin includes progesterone.

In an embodiment, the estrogen includes estradiol.

In an embodiment, culturing includes culturing for a period lasting between 3 and 30 days.

There is also provided, in accordance with an embodiment of the present invention, a method for use with extracted blood, including:
applying blood to a first gradient suitable for selecting first-pass cells having a density less than 1.077 g/ml;
applying the first-pass cells to a second gradient suitable for selecting second-pass cells having a density between 1.055 and 1.074 g/ml;
during a hypercapnic time period lasting at least 2 hours, culturing the second-pass cells under hypercapnic conditions, the hypercapnic time period characterized by a $CO_2$ level of greater than 5%;
during a non-hypercapnic time period lasting at least 1 day, culturing the second-pass cells under non-hypercapnic conditions, the non-hypercapnic time period characterized by a $CO_2$ level of less than or equal to 5%; and
identifying progenitor cells in the cultured cells.

In an embodiment, setting the $CO_2$ level during the hypercapnic time period to be at least 6%.

In an embodiment, the hypercapnic and non-hypercapnic time-periods are within a culturing time period lasting less than 30 days, and wherein culturing the second-pass cells under hypercapnic conditions includes culturing the second-pass cells under hypercapnic conditions during a first two days of the culturing time period.

In an embodiment, the hypercapnic and non-hypercapnic time-periods are within a culturing time period lasting less than 30 days, and wherein culturing the second-pass cells under hypercapnic conditions includes culturing the second-pass cells under hypercapnic conditions during a last two days of the culturing time period.

In an embodiment, the hypercapnic and non-hypercapnic time-periods are within a culturing time period lasting less than 30 days, and wherein culturing the second-pass cells under hypercapnic conditions includes culturing the second-pass cells under hypercapnic conditions for at least 2 hours between a first two days and a last two days of the culturing time period.

In an embodiment, culturing the second-pass cells under hypercapnic conditions is performed prior to culturing the second-pass cells under non-hypercapnic conditions.

In an embodiment, culturing the second-pass cells under hypercapnic conditions is performed following culturing the second-pass cells under non-hypercapnic conditions.

There is also provided, in accordance with an embodiment of the present invention, method for use with extracted blood, including:
applying blood to a first gradient suitable for selecting first-pass cells having a density less than 1.077 g/ml;
applying the first-pass cells to a second gradient suitable for selecting second-pass cells having a density between 1.055 and 1.074 g/ml;
culturing the second-pass cells in a culture medium including at least one agent selected from the list consisting of: erythropoietin, VEGF, IGF, FGF, estrogen, 17-β-estradiol, estrone, estriol, an estradiol derivative, estradiol valerate, estradiol cypionate, mestranol, quinestrol, progestin, a molecule from the progestin family, progesterone, synthetic progesterone, hydroxyprogesterone caroate, medroxyprogesterone acetate, a statin, simvastatin, atorvastatin, an anti-diabetic agent, and rosiglitazone; and
identifying progenitor cells in the cultured cells.

There is also provided, in accordance with an embodiment of the present invention, a method for use with extracted stem cells, including:
applying tissue including the stem cells to a first gradient suitable for selecting first-pass cells having a density less than 1.077 g/ml;
applying the first-pass cells to a second gradient suitable for selecting second-pass cells having a density between 1.055 and 1.074 g/ml;
increasing the number of cells having a density between 1.055 and 1.074 g/ml, by culturing the second-pass cells for a period lasting between 3 and 30 days; and
identifying progenitor cells in the cultured cells.

In an embodiment, applying the tissue includes applying umbilical cord blood to the first gradient.

In an embodiment, applying the tissue includes applying embryonic cells to the first gradient.

In an embodiment, applying the tissue includes applying placental cells to the first gradient.

In an embodiment, applying the tissue includes applying fetal cells to the first gradient.

In an embodiment, extracting the stem cells from bone marrow.

In an embodiment, mobilizing the stem cells from bone marrow to facilitate extraction of the stem cells.

In an embodiment, extracting the stem cells from peripheral blood.

In an embodiment, culturing the second-pass cells includes:

culturing the second-pass cells in a first container during a first portion of the period;

removing at least some of the second-pass cells from the first container at the end of the first portion of the period; and culturing, in a second container during a second portion of the period, the cells removed from the first container.

In an embodiment, removing the at least some of the second-pass cells includes selecting for removal cells that adhere to a surface of the first container.

In an embodiment, removing the at least some of the second-pass cells includes selecting for removal cells that do not adhere to a surface of the first container.

In an embodiment, the first container includes on a surface thereof a growth-enhancing molecule, and wherein culturing the cells in the first container includes culturing the cells in the first container that includes the growth-enhancing molecule.

In an embodiment, the growth-enhancing molecule is selected from the list consisting of: plasma, collagen, fibronectin, a growth factor and an antibody to a stem cell surface receptor.

In an embodiment, the second container includes on a surface thereof a growth-enhancing molecule, and wherein culturing the cells in the second container includes culturing the cells in the second container that includes the growth-enhancing molecule.

In an embodiment, the growth-enhancing molecule is selected from the list consisting of: plasma, collagen, fibronectin, a growth factor and an antibody to a stem cell surface receptor.

There is also provided, in accordance with an embodiment of the present invention, a method for treating a condition, including applying endothelial progenitor cells (EPCs) to a vicinity of tissue or a space of a subject selected from the list consisting of: tissue of a peripheral nerve of the subject, tissue of a central nervous system nerve of the subject, an optic nerve of the subject, choroid tissue of the subject, retinal tissue of the subject, sub-retinal space of the subject, corneal tissue of a subject, kidney tissue of the subject, tissue of a damaged bone of the subject, tissue of a fractured bone of the subject, inflamed tissue of the subject, infected tissue of the subject, contused tissue of the subject, damaged, ulcerated or wounded tissue of a skin of, brain tissue of the subject, tissue of a limb of the subject, tissue of a skin graft, and tissue of a reattached severed limb of the subject.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and increasing the number of cells having a density between 1.055 and 1.074 g/ml, by culturing the second-pass cells for a period lasting between 3 and 30 days.

In an embodiment, the method includes generating the EPCs by:

applying tissue including the stem cells to a first gradient suitable for selecting first-pass cells having a density less than 1.077 g/ml;

applying the first-pass cells to a second gradient suitable for selecting second-pass cells having a density between 1.055 and 1.074 g/ml;

applying the second-pass cells to a third gradient suitable for selecting third-pass cells having a density between 1.055 and 1.068 g/ml; and increasing the number of cells having a density between 1.055 and 1.068 g/ml, by culturing the third-pass cells for a period lasting between 3 and 30 days.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells on a surface including an antibody.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells on a surface including a growth-enhancing molecule other than collagen or fibronectin.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells for a period lasting between 1 and 5 days in a culture medium including up to 5% serum.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells for a period lasting between 1 and 5 days in a culture medium including greater than 10% serum.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a low-serum time period, culturing the second-pass cells in a culture medium including less than 10% serum; and during a high-serum time period, culturing the second-pass cells in a culture medium including greater than or equal to 10% serum.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a hypoxic time period lasting at least 2 hours, culturing the second-pass cells under hypoxic conditions; and during a non-hypoxic time period lasting at least 1 day, culturing the second-pass cells under non-hypoxic conditions.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

during a hypercapnic time period lasting at least 2 hours, culturing the second-pass cells under hypercapnic conditions, the hypercapnic time period characterized by a $CO_2$ level of greater than 5%; and during a non-hypercapnic time period lasting at least 1 day, culturing the second-pass cells under non-hypercapnic conditions, the non-hypercapnic time period characterized by a $CO_2$ level of less than or equal to 5%.

In an embodiment, the method includes generating the EPCs by:

applying blood to a first gradient suitable for selecting first-pass cells having a density less than 1.077 g/ml;

applying the first-pass cells to a second gradient suitable for selecting second-pass cells having a density between 1.055 and 1.074 g/ml; and culturing the second-pass cells in a culture medium including at least one agent selected from the list consisting of: erythropoietin, estrogen, an estrogen-family molecule, 17-β-estradiol, estrone, estriol, an estradiol derivative, estradiol valerate, estradiol cypionate, mestranol, quinestrol, progestin, a progestin-family molecule, progesterone, synthetic progesterone, hydroxyprogesterone caroate, medroxyprogesterone acetate, a statin, simvastatin, atorvastatin, an antidiabetic agent, and rosiglitazone.

applying tissue including the stem cells to a first gradient suitable for selecting first-pass cells having a density less than 1.077 g/ml;

applying the first-pass cells to a second gradient suitable for selecting second-pass cells having a density between 1.055 and 1.074 g/ml; and increasing the number of cells having a density between 1.055 and 1.074 g/ml, by culturing the second-pass cells for a period lasting between 3 and 30 days.

There is also provided, in accordance with an embodiment of the present invention, a method for use with extracted blood, including:

applying blood to a first gradient suitable for selecting first-pass cells having a density less than 1.077 g/ml;

applying the first-pass cells to a second gradient suitable for selecting second-pass cells having a density between 1.055 and 1.074 g/ml;

increasing the number of cells having a density between 1.055 and 1.074 g/ml, by culturing the second-pass cells for a period lasting between 1 and 30 days; and identifying progenitor cells in the cultured cells.

In an embodiment, the progenitor cells include endothelial progenitor cells (EPCs), and wherein identifying the progenitor cells includes identifying the EPCs.

There is also provided, in accordance with an embodiment of the present invention, a method for use with extracted blood, including:

applying blood to a first gradient suitable for selecting first-pass cells having a density less than 1.077 g/ml;

dividing the first-pass cells into respective first and second portions thereof;

applying the first portion of the first-pass cells to a second gradient suitable for selecting second-pass cells having a density between 1.055 and 1.074 g/ml;

mixing the second portion of the first-pass cells with the cells having a density between 1.055 and 1.074 g/ml;

increasing the number of cells having a density between 1.055 and 1.074 g/ml, by culturing the second-pass cells for a period lasting between 3 and 30 days; and identifying progenitor cells in the cultured cells.

In an embodiment, dividing the first-pass cells includes setting the first portion to be larger than the second portion.

In an embodiment, dividing the first-pass cells includes setting the first portion to be smaller than the second portion.

There is also provided, in accordance with an embodiment of the present invention, a method for use with extracted blood, including:

applying blood to a gradient to select cells having a first desired density range;

increasing the number of cells having a second desired density range by culturing the selected cells for a period lasting between 3 and 30 days; and identifying progenitor cells in the cultured cells.

In an embodiment, applying the blood to the gradient includes applying blood to a gradient suitable for selecting cells having a density less than 1.077 g/ml.

In an embodiment, applying the blood to the gradient includes applying blood to a gradient suitable for selecting cells having a density between 1.055 and 1.074 g/ml.

In an embodiment, increasing the number of cells includes culturing the cells for a period lasting between 4 and 8 days.

In an embodiment, applying the blood to the gradient includes applying the blood to a solution including a copolymer of sucrose and epichlorohydrin.

In an embodiment, applying the blood to the gradient includes applying the blood to a gradual density solution including polyvinylpyrrolidone-coated silica colloids.

In an embodiment, applying the blood to the gradient includes applying the blood to an aqueous solution of iodixanol.

In an embodiment, applying the blood cells to the gradient includes applying the blood cells to a FICOLL like gradient.

In an embodiment, applying the blood to the gradient includes applying the blood to an OPTIPREP like gradient.

In an embodiment, applying the blood to the gradient includes applying the blood to a PERCOLL like gradient.

There is also provided, in accordance with an embodiment of the present invention, a method for use with extracted blood, including:

applying blood to a gradient to select cells having a desired density range;

culturing the selected cells for a period lasting between 3 and 30 days on a surface including autologous plasma; and identifying progenitor cells in the cultured cells.

There is also provided, in accordance with an embodiment of the present invention, a method for use with extracted blood, including:

applying blood to a gradient to select cells having a desired density range;

culturing the selected cells on a surface including an antibody; and identifying progenitor cells in the cultured cells.

In an embodiment, culturing includes culturing the cells on the surface, when the surface is coated with autologous plasma.

In an embodiment, culturing includes culturing the cells on the surface, when the surface is coated with at least one plasma selected from the list consisting of: allogeneic plasma and xenogeneic plasma.

There is also provided, in accordance with an embodiment of the present invention, a method for use with extracted blood, including:

applying blood to a gradient to select cells having a desired density range;

culturing the selected cells on a surface including a growth-enhancing molecule other than collagen or fibronectin; and identifying progenitor cells in the cultured cells.

In an embodiment, culturing the cells includes culturing the cells on a surface that includes, in addition to the growth-enhancing molecule, at least one of: collagen and fibronectin.

There is also provided, in accordance with an embodiment of the present invention, a method for use with extracted blood, including:

applying blood to a gradient to select cells having a desired density range;

culturing the selected cells a period lasting between 1 and 5 days in a culture medium including up to 5% serum; and identifying progenitor cells in the cultured cells.

There is also provided, in accordance with an embodiment of the present invention, a method for use with extracted blood, including:

applying blood to a gradient to select cells having a desired density range;

culturing the selected cells for a period lasting between 1 and 5 days in a culture medium including greater than 10% serum; and identifying progenitor cells in the cultured cells.

In an embodiment, culturing the cells includes culturing the cells in a culture medium including less than 20% serum.

There is also provided, in accordance with an embodiment of the present invention, a method for use with extracted blood, including:

applying blood to a gradient to select cells having a desired density range;

during a low-serum time period, culturing the selected cells in a culture medium including less than 10% serum;

during a high-serum time period, culturing the selected cells in a culture medium including greater than or equal to 10% serum; and identifying progenitor cells in the cultured cells.

In an embodiment, culturing the cells during the low-serum time period includes culturing the cells in a culture medium including up to 5% serum.

In an embodiment, culturing the cells during the low-serum time period includes culturing the cells in a serum-free culture medium.

In an embodiment, culturing the cells during the low-serum time period includes culturing the cells for a duration of between 1 and 5 days.

In an embodiment, culturing the cells during the high-serum time period includes culturing the cells for a duration of between 1 and 30 days.

In an embodiment, culturing the cells during the low-serum time period is performed prior to culturing the cells during the high-serum time period.

In an embodiment, culturing the cells during the low-serum time period is performed following culturing the cells during the high-serum time period.

There is also provided, in accordance with an embodiment of the present invention, a method for use with extracted blood, including:

applying blood to a gradient to select cells having a desired density range;

during a hypoxic time period lasting at least 2 hours, culturing the selected cells under hypoxic conditions;

during a non-hypoxic time period lasting at least 1 day, culturing the selected cells under non-hypoxic conditions; and identifying progenitor cells in the cultured cells.

In an embodiment, the hypoxic and non-hypoxic time-periods are within a culturing time period lasting less than 30 days, and wherein culturing the cells under hypoxic conditions includes culturing the cells under hypoxic conditions during a first two days of the culturing time period.

In an embodiment, the hypoxic and non-hypoxic time-periods are within a culturing time period lasting less than 30 days, and wherein culturing the cells under hypoxic conditions includes culturing the cells under hypoxic conditions during a last two days of the culturing time period.

In an embodiment, the hypoxic and non-hypoxic time-periods are within a culturing time period lasting less than 30 days, and wherein culturing the cells under hypoxic conditions includes culturing the cells under hypoxic conditions for at least 2 hours between a first two days and a last two days of the culturing time period.

In an embodiment, culturing the cells under hypoxic conditions is performed prior to culturing the cells under non-hypoxic conditions.

In an embodiment, culturing the cells under hypoxic conditions is performed following culturing the cells under non-hypoxic conditions.

There is also provided, in accordance with an embodiment of the present invention, a method for use with extracted blood, including:

applying blood to a gradient to select cells having a desired density range;

during a hypercapnic time period lasting at least 2 hours, culturing the selected cells under hypercapnic conditions, the hypercapnic time period characterized by a $CO_2$ level of greater than 5%;

during a non-hypercapnic time period lasting at least 1 day, culturing the selected cells under non-hypercapnic conditions, the non-hypercapnic time period characterized by a $CO_2$ level of less than or equal to 5%; and identifying progenitor cells in the cultured cells.

In an embodiment, the method includes setting the $CO_2$ level during the hypercapnic time period to be at least 6%.

In an embodiment, the hypercapnic and non-hypercapnic time-periods are within a culturing time period lasting less than 30 days, and wherein culturing the cells under hypercapnic conditions includes culturing the cells under hypercapnic conditions during a first two days of the culturing time period.

In an embodiment, the hypercapnic and non-hypercapnic time-periods are within a culturing time period lasting less than 30 days, and wherein culturing the cells under hypercapnic conditions includes culturing the cells under hypercapnic conditions during a last two days of the culturing time period.

In an embodiment, the hypercapnic and non-hypercapnic time-periods are within a culturing time period lasting less than 30 days, and wherein culturing the cells under hypercapnic conditions includes culturing the cells under hypercapnic conditions for at least 2 hours between a first two days and a last two days of the culturing time period.

In an embodiment, culturing the cells under hypercapnic conditions is performed prior to culturing the cells under non-hypercapnic conditions.

In an embodiment, culturing the cells under hypercapnic conditions is performed following culturing the cells under non-hypercapnic conditions.

There is also provided, in accordance with an embodiment of the present invention, a method for use with extracted blood, including:

applying blood to a gradient to select cells having a first desired density range;

culturing the selected cells in a culture medium including at least one agent selected from the list consisting of: VEGF, IGF, FGF, erythropoietin, estrogen, an estrogen-family molecule, 17-β-estradiol, estrone, estriol, an estradiol derivative, estradiol valerate, estradiol cypionate, mestranol, quinestrol, progestin, a progestin-family molecule, progesterone, synthetic progesterone, hydroxyprogesterone caroate, medroxyprogesterone acetate, a statin, simvastatin, atorvastatin, an antidiabetic agent, and rosiglitazone; and identifying progenitor cells in the cultured cells.

In an embodiment, the progenitor cells include endothelial progenitor cells (EPCs), and wherein identifying the progenitor cells includes identifying the EPCs.

In an embodiment, applying the blood to the gradient includes applying blood to a gradient suitable for selecting cells having a density less than 1.077 g/ml.

In an embodiment, applying the blood to the gradient includes applying blood to a gradient suitable for selecting cells having a density between 1.055 and 1.074 g/ml.

There is also provided, in accordance with an embodiment of the present invention, a method for use with extracted stem cells, including:

applying tissue including the stem cells to a gradient to select cells having a first desired density range;

increasing the number of cells having a second desired density range, by culturing the selected cells for a period lasting between 3 and 30 days; and identifying progenitor cells in the cultured cells.

In an embodiment, applying the tissue includes applying umbilical cord blood to the gradient.

In an embodiment, applying the tissue includes applying embryonic cells to the gradient.

In an embodiment, applying the tissue includes applying fetal cells to the gradient.

In an embodiment, applying the tissue includes applying placental cells to the gradient.

In an embodiment, the method includes extracting the stem cells from bone marrow.

In an embodiment, the method includes mobilizing the stem cells from bone marrow to facilitate extraction of the stem cells.

In an embodiment, the method includes extracting the stem cells from blood.

In an embodiment, the method includes culturing the cells includes:

culturing the cells in a first container during a first portion of the period;

removing at least some of the cells from the first container at the end of the first portion of the period; and culturing, in a second container during a second portion of the period, the cells removed from the first container.

In an embodiment, the method includes removing the at least some of the cells includes selecting for removal cells that adhere to a surface of the first container.

In an embodiment, removing the at least some of the cells includes selecting for removal cells that do not adhere to a surface of the first container.

In an embodiment, the first container includes on a surface thereof a growth-enhancing molecule, and wherein culturing the cells in the first container includes culturing the cells in the first container that includes the growth-enhancing molecule.

In an embodiment, the growth-enhancing molecule is selected from the list consisting of: plasma, collagen, fibronectin, a growth factor and an antibody to a stem cell surface receptor.

In an embodiment, the second container includes on a surface thereof a growth-enhancing molecule, and wherein culturing the cells in the second container includes culturing the cells in the second container that includes the growth-enhancing molecule.

In an embodiment, the growth-enhancing molecule is selected from the list consisting of: plasma, collagen, fibronectin, a growth factor and an antibody to a stem cell surface receptor.

DETAILED DESCRIPTION OF EMBODIMENTS

In accordance with an embodiment of the present invention, a method is provided for isolating, differentiating, and growing endothelial progenitor cells (EPCs) from human peripheral blood. The EPCs are typically implanted in a patient to induce vasculogenesis and/or angiogenesis and/or neovascularization. Typically, peripheral blood mononuclear cells (PBMCs) separated by a density gradient such as Ficoll are further enriched by one or more other density gradients (such as PERCOLL, OPTIPREP OR NYCODENTZ), and are then allowed to adhere to tissue culture dishes. Cells are typically grown for 3-30 days in an enriched culture medium. At several time points during the culture period, samples are taken for phenotypic assessment. Expanded cells are collected and saved until implantation into the patient.

A series of protocols are described hereinbelow which may be used separately or in combination, as appropriate, in accordance with embodiments of the present invention. It is to be appreciated that numerical values are provided by way of illustration and not limitation. Typically, but not necessarily, each value shown is an example selected from a range of values that is within 25% of the value shown. Similarly, although certain steps are described with a high level of specificity, a person of ordinary skill in the art will appreciate that other steps may be performed, mutatis mutandis.

Protocol for Tissue Culture Dish Coating

Suitable containers, such as culture dishes, may be coated with one or a combination of EPC-growth-enhancing molecules. The molecules may comprise antibodies to progenitor cell surface receptors such as CD34, CD133, Tie-2, VEGFR-2 (KDR), CD144 or molecules such as LDL, VEGF, FGF, IGF, or platelet-derived growth factor (PDGF).

Example 1

Coating T-75 Flasks with Autologous Plasma

For 20 T-75 flasks: Prepare on the day of cell preparation

Coating of T-75 Flasks surface with the plasma can be done using autologous plasma removed from the centrifuged tissue sample, or alternatively, with plasma from a different source, such as plasma commercially available from Chemicon of Temecula, Calif., US.

Collect plasma from the upper fraction of FICOLL tubes.
Fill each flask with 2-5 ml plasma.
Incubate at 37° C. for at least 30 min.
Discard plasma.
Wash flask twice in 10 ml PBS.
Flasks are ready for use.

Example 2

Coating T-75 Flasks with 25 µg/ml Fibronectin

For 20 T-75 flasks: Prepare (a) on the day of cell preparation, or (b) one day before the day of cell preparation.

Prepare 50 ml of 25 µg/ml Fibronectin solution in PBS.
Add 250 µl Fibronectin 5 mg/ml to 50 ml PBS
Fill each flask with 2-5 ml Fibronectin 25 µg/ml.
Incubate at 37° C. for at least 30 min.
Collect Fibronectin solution.
Fibronectin solution can be re-used if stored in sterile 50 ml tube at 4° C., typically for up to 1 week.
Wash flask twice in PBS.
Keep dry flasks at room temperature.
Dried flasks can be saved for one week at room temperature (RT).

Example 3

Coating T-75 Flasks with Fibronectin and 5 µg/ml Anti-CD34

For 20 T-75 flasks: Prepare (a) on the day of cell preparation, or (b) one day before the day of cell preparation.
Coat flasks with Fibronectin, as described in Example 1.
Prepare 25 ml of 5 µg/ml Anti-CD34 solution in PBS.
Add 125 µl anti-CD34 1 mg/ml to 25 ml PBS.
Fill each flask with 5 ml anti-CD34 5 µg/ml.
Incubate for 2 h at 37° C. or over night at 4° C.
Withdraw antibody solution.
Wash flask twice in PBS.
Flasks are ready for use.
Cell Preparation
Mix the blood by gently flipping the blood bag up and down.
Transfer blood from bag into a sterile 500 ml bottle.
Load blood onto a FICOLL gradient.
Fill tubes with blood up to 50 ml.
Spin the tubes for 20 minutes at 1050 g at room temperature with no brake.
Collect most of the plasma from the upper layer in empty 50 ml tubes.
Collect the white blood cell ring (e.g., the PBMC) fraction from every tube.
Transfer each PBMC to a new 50 ml tube, pre-filled with 15-20 ml of PBS.
Adjust volume to 30 ml per tube using PBS.
Spin tubes for 15 minutes at 580 g, at room temperature, and discard the supernatant.
Gently mix cell pellet and re-suspend with 1-5 ml PBS.
Combine the contents of every four tubes into one 50 ml tube, and fill that tube up to 50 ml with PBS.
For example:
(1) Prepare OptiPrep Gradient of 1.072 g/ml.
(1) Prepare OPTIPREP gradient of 1.072 g/ml.
For 36 ml OPTIPREP gradient of 1.072 g/ml.
Prepare gradient of 1.072 g/ml by mixing together: (i) 25 ml solution of 0.5% human or bovine serum albumin, 0.8% NaCl, 10 mM Hepes, 1 mM EDTA (buffered to pH 7.4) with (ii) 11 ml mixture of 10 ml OPTIPREP solution+5 ml solution of 0.5% human or bovine serum albumin, 0.8% NaCl, 10 mM Hepes, 1 mM EDTA (buffered to pH 7.4).
Mix together: (a) 10 ml cells derived from the Cell Preparation steps described above, with (b) 10 ml mixture of 10 ml OPTIPREP solution+5 ml solution of 0.5% human or bovine serum albumin, 0.8% NaCl, 10 mM Hepes, 1 mM EDTA (buffered to pH 7.4).
Place on top of the mixture of (a) and (b) 20 ml of the OPTIPREP gradient of 1.072 g/ml prepared in steps (i) and (ii), and place on top of this 1.5 ml solution of 0.5% human or bovine serum albumin, 0.8% NaCl, 10 mM Hepes, 1 mM EDTA (buffered to pH 7.4).

Centrifuge 30 minutes at 700 g, e.g., at room temperature or 4° C., with no brake.
Collect the isolated cells from the interface between the gradient and solution of 0.5% bovine serum albumin, 0.8% NaCl, 10 mM Hepes, 1 nM EDTA, pH 7.4.
Centrifuge 10 minutes at 395 g, at room temperature.
Discard supernatant and re-suspend pellet in 10 ml culture medium.
(2) Prepare PERCOLL Gradient for Cell Density of 1.060-1.068 g/ml. For example, for 30 ml continuous PERCOLL gradient preparation mix in 50 ml tube: 13.5 ml PERCOLL (Amersham).
15.0 ml MEM Spinner modification
1.5 ml 10× Earle's salts solution
Centrifuge 10 min at 14000×g without brakes in a fixed angle rotor.
Carefully take the gradient out of the rotor. The gradient is ready to use now.
The tube should be able to resist centrifugation at 14000×g.
Apply all the cells on the PERCOLL gradient.
Centrifuge 30 min at 400×g without brakes.
Collect enriched PBMCs and transfer into a 50 ml tube.
Fill the tube with PBS, centrifuge 10 min at 300×g.
Resuspend in 50 ml PBS, centrifuge 10 min at 200×g.
Resuspend in 50 ml PBS, centrifuge 10 min at 200×g.
Take a 50 µl sample for cell counting.
Serum Preparation
Serum can be obtained directly from the patient's coagulated plasma ("off the clot" serum), or prepared from plasma generated from blood pre-treated with an anticoagulant.
For example, for preparation of serum from blood pre-treated with an anticoagulant:
Take plasma that was collected from the upper fraction of FICOLL tubes (See above description of Cell Preparation).
For each 50 ml plasma, add 1.2 ml 0.8M $CaCl_2 2H_2O$ or any other chemical/biological clotting inducer such as Calcium Chloride, Thromboplastin, Thrombin agonist peptides or others, in order to catalyze the clotting mechanism.
Incubate for 0.5-4 hrs at 37° C.
Spin coagulated plasma for 10 minutes at 3500 g.
Collect the serum in a new tube. Do not allow the clot to mix with the serum.
Use collected serum for medium preparation, or aliquot and save at −20° C. until use.
Cell Counting
Pre-fill four 96 w plates with 50 µl Trypan blue (TB) each.
Make 1:5 dilutions by transfer of 20 µl of cells sample to one TB containing well, and mix gently by pipetting up and down.
Load 10 µl of diluted cells onto each of the 2 chambers of hemocytometer.
Count clear (viable) and blue (dead) cells that lay in the central 25 squares of the upper and lower chambers.
If fewer than 10 cells are counted, make 1:2 dilution by transfer of 50 µl of cells sample to 50 µl TB.
If more than 200 cells are counted, make 1:25 dilution by transfer of 20 µl of 1:5 suspensions to one TB-containing well, and mix gently by pipetting up and down.
Calculate cell number for each chamber according to the following equation:

No. of viable cells×10,000×Dilution factor=No. of viable cells/ml

No. of dead cells×10,000×Dilution factor=No. of dead cells/ml

% Dead cells=No. of Dead cells/(No. of Viable cells+ No. of Dead cells)×100

% of dead cells should not typically exceed 30%.
Calculate average cell number.
Record counting results.
Summarize final cell numbers and yield of cells/ml blood.
Medium Preparation
Calculate the volume of needed medium
Prepare culture medium.
Medium should contain 1-20% autologous serum.

Medium can contain the following additives in various concentrations of 0.5 pg/ml-1 ng/ml, or 1 ng/ml-100 g/ml, for example, EPO (0.01-10 IU/ml), IGF (1-100 ng/ml), FGF 10-100 ng/ml, VEGF (0.5-20 ng/ml); Heparin 5-100 IU/ml; different molecules depends on their weight and the desired molarity can range from pg-µg, or the corresponding molarity: Statin molecules (e.g. simvastatin 5-500 µg/ml), antidiabetic agents (e.g., Rosiglitazone 5-500 µg/ml), and/or steroid hormones such as an estrogen (e.g., 17-β-estradiol (2-200 ng/ml) and a progestin (e.g. progesterone 2-2000 ng/ml), and combinations thereof.

It is hypothesized that the steroid reproductive system hormones (e.g., estrogens and progestins) exert their effect by elevating EPC blood levels. Thus, applying such molecules or any combination thereof can increase the yield of the production or the differentiation of the progenitors into EPCs in vitro, particularly when cells from peripheral blood are subjected to their effects.

Example for Low % Serum Medium
For 100 ml medium add:
2 µl of VEGF 100 g/ml (final concentration of 10 µg/ml)
100 µl of Heparin 5000 U/ml (final concentration of 5 U/ml)
5 ml Autologous Serum
94.9 ml serum-free medium
Example 1 for High % Serum Medium
For 100 ml medium add:
2 µl of VEGF 100 µg/ml (final concentration of 10 µg/ml)
100 µl of Heparin 5000 U/ml (final concentration of 5 U/ml)
20 ml Autologous Serum
79.9 ml serum-free medium
Example 2 for High % Serum Medium
For 100 ml medium add:
5 µl of VEGF 100 µg/ml (final concentration of 10 µg/ml)
100 µl of Heparin 5000 U/ml (final concentration of 5 U/ml)
4 µl of Progesterone 5 mg/ml (final concentration of 0.2 µg/ml)
10 ml Autologous Serum
89.9 ml serum-free medium
Example 3 for High % Serum Medium
For 100 ml medium add:
5 µl of VEGF 100 µg/ml (final concentration of 10 µg/ml)
100 µl of Heparin 5000 U/ml (final concentration of 5 U/ml)
4 µl of 17-β-Estradiol 0.05 mg/ml (final concentration of 0.002 µg/ml)
10 ml Autologous Serum
89.9 ml serum-free medium
Example 3 for High % Serum Medium
For 100 ml medium add:
5 µl of VEGF 100 µg/ml (final concentration of 10 µg/ml)
100 µl of Heparin 5000 U/ml (final concentration of 5 U/ml)
4 µl of Progesterone 0.05 mg/ml (final concentration of 0.002 µg/ml)
4 µl of 17-β-Estradiol 0.005 mg/ml (final concentration of 0.0002 µg/ml)
10 ml Autologous Serum
89.9 ml serum-free medium
Example 4 for High % Serum Medium
For 100 ml medium add:
2 µl of VEGF 100 µl/ml (final concentration of 10 µg/ml)
100 µl of Heparin 5000 U/ml (final concentration of 5 U/ml)
330 µl of Simvastatin 570 µM (final concentration of 0.95 µM)
10 ml Autologous Serum
89.6 ml serum-free medium Culturing
Split cells from the combined cell suspension.
Spin tubes for 15 minutes at 500 g, room temperature, discard the supernatant.
Gently mix cell pellet and re-suspend cells to $5-50 \times 10^6$/ml.
Seed $1-5 \times 10^6$ cells/ml.
Incubate flasks at 37° C., 5% $CO_2$.
Incubate cells in medium containing low serum levels (e.g., up to 5%). Alternatively or additionally, use high (>10%) serum levels.

In accordance with an embodiment of the present invention, the cells are incubated in low-serum medium prior to being incubated in high-serum medium.

Alternatively, the cells are incubated in low-serum medium following being incubated in high-serum medium.

In accordance with an embodiment, (a) incubation in medium comprising 0.5%-5% serum is carried out before incubation in high-serum medium (>10% serum), and (b) incubation in serum-free medium is carried out (i) before the incubation in the 0.5%-5% serum medium, (ii) between the incubation in the medium comprising 0.5%-5% serum and the incubation in the high-serum medium, and/or (iii) following the incubation in the high-serum medium.

Alternatively, (a) incubation in medium comprising 0.5%-5% serum is carried out after incubation in high-serum medium (>10% serum), and (b) incubation in serum-free medium is carried out (i) following the incubation in the 0.5%-5% serum medium, (ii) between the incubation in the high-serum medium and the incubation in the medium comprising 0.5%-5% serum, and/or (iii) before the incubation in the high-serum medium.

In an embodiment, techniques described herein with respect to low-serum medium are carried out using serum-free medium.

Increased expansion and differentiation of cells may be obtained by exposure of the cell culture to hypoxia and/or hypercapnia (H/H) for 2-12 hours, 12-24 hours, 24-36 hours, or 36-48 hours. This is done one or more times at different points during cell culturing. (See below for a sample applied hypoxia protocol.)

In the context of the present patent application and in the claims, the term hypercapnia refers to a concentration of $CO_2$ that is greater than 5%.

After the first three days of culture, the cells are grown in a medium containing high levels of serum (e.g., >10%).
Examinations of culture morphology are performed.
Refreshment of medium is performed every 2-3 days.
For example, when cells are cultured in T-75 Flasks:
1. Collect cells in 50 ml tubes.
2. Fill every flask with 5 ml fresh medium.
3. Spin tubes for 10 minutes at 450 g, room temperature, discard the supernatant.
4. Gently mix cell pellet and resuspend cells in 5 ml fresh medium per flask.
5. Return 5 ml of cell suspension to every flask.

6. Sample cells for fluorescence-activated cell sorting (FACS) and/or immunohistological analysis every few days (for example, on days 6, 9, 13, 16, 20, 24 and 30).
7. Follow and record culture morphology whenever culture is treated.
8. Sample culture medium from growth dishes for sterility tests at the beginning and end of the procedure, and every 10 days during the culture period.
9. Collect all cultured cells (See section below, "Collection of cells for FACS staining").

Applied Hypoxia and/or Hypercapnia

For some applications, increased expansion and differentiation of cells may be obtained by exposure of the cell culture, for 2-48 hours, to hypoxic conditions (e.g., 1-5% or 5-15% oxygen) and/or to hypercapnic conditions (e.g., 6-10% $CO_2$). This is typically done one or more times, at different points during cell culturing.

For example:

On the first day of culture, incubate T-75 flasks in an oxygen controlled incubator. Set the oxygen pressure at 5% and/or set the $CO_2$ concentration to greater than 5% (e.g., 6%-8%, or 8%-10%), and maintain it at this level for 6 hours. Remove the flasks from the incubator and examine the culture. Take a sample of cells and test viability by Trypan blue exclusion method. Set the oxygen pressure of the incubator at 21% and/or set the $CO_2$ concentration to 5%. Re-insert the flasks into the incubator and continue incubation for the rest of the period. This procedure can be repeated, for example, once a week during the culture period and/or within 24, 48, or 72 hours before termination of the culture.

In an embodiment, cells are cultured in hypercapnic conditions prior to being cultured in an environment of less than or equal to 5% $CO_2$. Alternatively or additionally, cells are cultured in hypercapnic conditions following being cultured in an environment of less than or equal to 5% $CO_2$.

Reseeding of Adherent and/or Detached and/or Floating Cells

For example:

For some applications, increased expansion and differentiation of cells may be achieved by re-seeding collected cells on new pre-coated dishes in culture medium.

On the third or fourth day of culture, collect all cultured cells. (See section below, "Collection of cells for FACS staining.") Spin tubes for 10 minutes at 450 g, at room temperature. Discard the supernatant. Then, gently mix pellet and re-suspend cells in 10 ml fresh medium per flask. Finally, seed suspended cells in new pre-coated T-75 flasks. Continue culturing the cells, and perform all other activities (e.g., medium refreshment, visual inspection, and/or flow cytometry), as appropriate, as described herein.

This procedure can be performed weekly during the culture period and/or within 24, 48, or 72 hours before termination of the culture.

Cell Preservation

Cells can be kept in a preservation medium or frozen in freezing buffer until use, e.g., implantation into the patient.

Collection of Cells for FACS Staining

Collect cells in 50 ml tubes.

Carefully wash flask surface by pipetting with cold PBS, to detach adherent cells.

Collect washed adherent cells in 50 ml tubes.

Add 5 ml of cold PBS.

Detach remaining adherent cells using gentle round movements with cell scraper.

Collect the detached cells and add them to the tube.

As appropriate, add 5 ml EDTA and incubate at 37° C. for 5 minutes. Collect the detached cells and add them to the tube.

Spin tube for 5 minutes at 450 g, room temperature. Re-suspend the pellet in 2-5 ml PBS.

Count the cells and record counting results.

Summarize final cell numbers and yields/number of seeded cells for every operation day.

Divide equal volumes of cells to FACS.

FACS Staining

Wash cells with PBS.

Spin tubes for 5 minutes at 450 g, 4-8° C.

Totally discard the supernatant by pouring the buffer and absorbing remainder on tissue.

Gently mix cell pellet.

Add staining reagent (according to staining table) and mix cells pellet.

Incubate tubes for 15-30 min on ice water in the dark.

Wash the cells with PBS.

Spin tubes for 5 minutes at 450 g, 4-8° C.

Totally discard the supernatant by pouring the buffer and absorbing remainder on tissue.

Gently mix cell pellet.

Add 0.5 ml PBS per tube (or less, if tube contains less than $1 \times 10^6$ cells).

If aggregates are visible, transfer cell suspension through 200 μm mesh.

Read staining results using FACS machine.

Summarize and record FACS results.

Colony Formation Test

1. Collect cultured cells. (See section, "Collection of cells for FACS staining.")
2. Suspend $100 \times 10^3$ cells in 0.7 ml enriched medium containing 50 ng/ml SCF, 2 IU/ml EPO, 5 ng/ml IL-3 and 25 mg/ml BTI-Endothelial cell growth supplement (ECGS) in M199.
3. To a round bottom tube add the following ingredients and mix gently;
   3.1. Methylcellulose 2%-1.4 ml
   3.2. FCS—0.9 ml
   3.3. Cell suspension 0.7 ml
4. Seed each mix of 3 ml into two 35 mm Petri dishes (1.5 ml in each).
5. Place both 35 mm Petri dishes in a 100 mm Petri dish containing another 35 mm Petri dish pre-filled with ddH2O
6. Incubate in 37° C., 5% $CO_2$, 97% humidity.
7. Score colonies after 10-14 days, using an inverted microscope Tube Formation Test 1. Thaw ECMatrix at 4 C overnight.
2. Add 100 microliters of 10× diluent buffer to 900 microliters of ECMatrix solution in a sterile microfuge tube.
3. Mix gently; do not pipette air into the solution. Keep solution on ice to avoid solidification.
4. Transfer 40 microliters buffered ECMatrix solution to each well of a 96-well tissue culture plate that has been pre-cooled at 4 C over night
5. Incubate at 37 C for at least 1 hour to allow the matrix solution to solidify.
6. Collect cultured cells. (See section, "Collection of cells for FACS staining.")
7. Suspend cells to $0.15 \times 10^6$/ml in enriched medium containing 10% Human serum, 25 micrograms/ml BTI-Endothelial cell growth supplement (ECGS) and 5 IU/ml heparin in M199
8. Pippette 150 microliter of cell suspension per well onto the surface of the polymerized ECMatrix.
9. Incubate overnight in 37° C., 5% $CO_2$, 97% humidity
10. Inspect tube formation under an inverted light microscope at 40×-200× magnification.

Cell Specifications

If the cells are to be transplanted into a human, then the following conditions should typically be met:

(I) Cells should be generally free from any bacterial or viral contamination.

(II) Cells should be morphologically characterized as (a) larger in size than lymphocytes and/or (b) elongated, spindle-shaped or irregular-shaped and/or (c) granulated or dark nucleated and/or (d) with flagella-like structures or pseudopodia and/or (e) fibroblast-like or polygonal in shape.

(III) Final cell suspension should generally contain at least $1 \times 10^6$ cells expressing one or more of the markers: CD31, and/or CD34, and/or CD133 and/or CD34+CD133, and/or KDR, and/or CD34+KDR, and/or CD144, and/or von Willebrand Factor, and/or SH2 (CD105), and/or SH3, and/or fibronectin, and/or collagen (types I, III and IV), and/or ICAM (type 1 or 2) and/or VCAM1 and/or Vimentin and/or BMP-R IA and/or BMP-RII and/or CD44 and/or integrin b1 and/or aSM-actin and/or MUC18 and/or be positive for the enzymatic reaction Dil-Ac-LDL.

Results Obtained in Accordance with Embodiments of the Present Invention

Example 1

Two-pass isolation of EPCs was carried out in seven independent experiments using FICOLL (first pass) and OPTIPREP (second pass), as described above. Results in Table 1 show enrichment of the percentage of CD34+ cells in the second-pass cells. Enrichment is defined as the percentage of CD34+ cells following the second pass divided by the percentage of CD34+ cells following the first pass using OPTIPREP.

TABLE 1

Enrichment of % CD 34 in the Second-Pass cells

| Experiment number | % CD34+ Cells | | Enrichment Factor |
|---|---|---|---|
| | First Pass | Second Pass | |
| 1 | 0.2 | 0.49 | 2.5 |
| 2 | <0.2 | 0.34 | >1.7 |
| 3 | <0.2 | 0.69 | >3.5 |
| 4 | <0.2 | 0.65 | >3.3 |
| 5 | <0.2 | 0.58 | >2.9 |
| 6 | <0.2 | <0.2 | — |
| 7 | <0.2 | 0.46 | >2.3 |

Example 1

In a set of separate experiments, the ability of first-pass enriched EPCs to generate tubes was evaluated using a tube-formation test following in-vitro growth on Fibronectin-coated T-75 Flasks in the presence of medium containing high serum levels (>10% autologous serum or non-autologous serum), 1, 2, 10 or 20 ng/ml VEGF, and 5-25 TU/ml Heparin. Typical tube formation images are presented in FIG. 1. In these experiments conducted with human blood, using the protocol described hereinabove, images were taken using an inverted microscope (Nikon ECLIPSE TS100) using amplifications of ×4 and ×20.

FIG. 1 shows tube formation test from first-pass EPCs enrichment in culture.

Example 2

In a set of separate experiments, enrichment of EPCs from second-pass cells was evaluated following in-vitro growth on Fibronectin-coated T-75 Flasks in the presence of medium containing autologous serum, VEGF, b-FGF, IGF, and Heparin. Flow-cytometry percentage staining results from twenty independent experiments are summarized in the Table for example 2. In these experiments conducted with human blood, using the protocol described hereinabove, FACS staining results of cells cultured in media containing high serum levels (>10%) and 1, 2, 10, or 20 ng/ml VEGF yielded the following changes in staining levels from day 0 to day 13:

Table for example 2 Enrichment of Second-Pass EPCs following thirteen days of culture

| Marker | % Stained cells on day 0 | % Stained cells on day 13 |
|---|---|---|
| CD45 | 85%-98% | 7.0%-39.0% |
| CD34 | Undetectable (<1%) | up to 17.7% |
| CD133 | Undetectable (<1%) | up to 6.5% |
| KDR | Undetectable (<0.5%) | up to 7.3% |

Example 3

In a set of separate experiments, enrichment of EPCs from first-pass cells was evaluated following in-vitro growth on Fibronectin-coated T-75 Flasks in the presence of medium containing autologous serum, VEGF, and Heparin. Flow-cytometry percentage staining results from independent experiments are summarized in the Table for example 3. These experiments were conducted with human blood, using the protocol described hereinabove. Before incubation the cells exhibited less than 1% CD34. FACS staining results of cells cultured in media containing 5-20% autologous serum (typically 10%); 1, 2, 10, or 20 ng/ml VEGF and 5-25 IU/ml Heparin are summarized. The following surface markers were analyzed: CD45 (a pan-lymphocyte marker), the stem/progenitor cell markers CD34 and CD117, and the EPC/endothelial cell markers CD133, KDR (VEGF-R), CD144, and Dil-Ac-LDL.

Table for example 3. Characterization of first-pass EPCs Cultured on Fibronectin pre-coated flasks in the presence of VEGF

| Marker | Average (%) | std. Error | N |
|---|---|---|---|
| CD45 | 89.36 | 0.85 | 83 |
| CD34 | 11.62 | 1.11 | 87 |
| CD117 | 7.01 | 1.09 | 45 |
| CD133 | 2.85 | 0.46 | 41 |
| KDR | 1.79 | 0.38 | 85 |
| CD144 | 10.33 | 1.50 | 3 |
| DIL-Ac-LDL | 7.97 | 0.42 | 3 |

Example 4

In a set of separate experiments, enrichment of EPCs from first-pass cells was evaluated following in-vitro growth on autologous plasma-coated T-75 Flasks in the presence of medium containing autologous serum, VEGF and Heparin. Flow-cytometry percentage staining results from 17 independent experiments are summarized in the Table for example 4. These experiments were conducted with human blood, using the protocol described hereinabove. Before incubation the cells exhibited less than 1% CD34. FACS staining results of cells cultured in media containing 5-20% autologous serum (typically 10%), 1, 2, 10, or 20 ng/ml VEGF and 5-25 IU/ml Heparin are summarized. The following surface markers were analyzed: CD45 (a pan-lymphocyte marker), the stem/progenitor cell markers CD34 and CD117, and the EPC/endothelial cell markers CD133 and KDR (VEGF-R).

Table for example 4. Characterization of first-pass EPCs cultured on plasma-coated flasks

| Marker | AVG | SE |
|---|---|---|
| CD45 | 89.46 | 1.75 |
| CD34 | 6.94 | 1.29 |
| CD117 | 4.25 | 0.72 |
| CD133 | 2.03 | 0.57 |
| KDR | 1.31 | 0.39 |

Example 5

In a set of separate experiments, enrichment of EPCs from first-pass cells was evaluated following in-vitro growth on autologous plasma-coated T-75 Flasks in the presence of medium containing autologous serum, VEGF, progesterone and Heparin. Flow-cytometry percentage staining results from 3 independent experiments are summarized in the Table for example 5. These experiments were conducted with human blood, using the protocol described hereinabove. Before incubation the cells exhibited less than 1% CD34. FACS staining results of cells cultured in media containing 5-20% autologous serum (typically 10%), 1, 2, 10, or 20 ng/ml VEGF, 0.02-2 microgram/ml progesterone and 5-25 IU/ml Heparin are summarized. The following surface markers were analyzed: CD45 (a pan-lymphocyte marker), the stem/progenitor cell markers CD34 and CD117, and the EPC/endothelial cell markers CD133 and KDR (VEGF-R).

Table for example 5. Characterization of first-pass EPCs cultured on plasma pre-coated flasks in the presence of progesterone

| Marker | AVG | SE |
|---|---|---|
| CD45 | 94.82 | 2.31 |
| CD34 | 21.22 | 3.47 |
| CD117 | 5.54 | 2.08 |
| CD133 | 5.72 | 0.47 |
| KDR | 1.05 | 0.12 |

Example 6

In a set of separate experiments, enrichment of EPCs from first-pass cells was evaluated following in-vitro growth on autologous plasma-coated T-75 Flasks in the presence of medium containing autologous serum, VEGF, 17-beta-estradiol and Heparin. Flow-cytometry percentage staining results from 3 independent experiments are summarized in the Table for example 6. These were experiments conducted with human blood, using the protocol described hereinabove. Before incubation the cells exhibited less than 1% CD34. FACS staining results of cells cultured in media containing 5-20% autologous serum (typically 10%), 1, 2, 10, or 20 ng/ml VEGF, 0.002-2 microgram/ml 17-β-Estradiol and 5-25 IU/ml Heparin are summarized. The following surface markers were analyzed: CD45 (a pan-lymphocyte marker), the stem/progenitor cell markers CD34 and CD117, and the EPC/endothelial cell markers CD133, and KDR (VEGF-R).

Table for example 6. Characterization of first-pass EPCs cultured on plasma pre-coated flasks in the presence of 17-β-estradiol

| Marker | average | SE |
|---|---|---|
| CD45 | 96.14 | 0.38 |
| CD34 | 4.12 | 0.05 |
| CD117 | 1.41 | 0.27 |
| CD133 | 1.77 | 0.88 |
| KDR | 0.28 | 0.20 |

Example 7

In a set of separate experiments, enrichment of EPCs from first-pass cells was evaluated following in-vitro growth on T-75 Flasks coated with plasma and anti-CD34 antibodies in the presence of medium containing autologous serum, VEGF and Heparin. Flow-cytometry percentage staining results from 2 independent experiments are presented in the Table for example 7. These were experiments conducted with human blood, using the protocol described hereinabove. Before incubation the cells exhibited less than 1% CD34. FACS staining results of cells cultured in media containing FACS staining results of cells cultured on T-75 flasks coated with 5 ml autologous plasma and 0.5-10 micrograms/ml anti-human CD34 in media containing 5-20% autologous serum (typically 10%), 1, 2, 10, or 20 ng/ml VEGF and 5-25 TU/ml Heparin are presented. The following surface markers were analyzed: CD45 (a pan-lymphocyte marker), the stem/progenitor cell markers CD34 and CD117, and the EPC/endothelial cell markers CD133 and KDR (VEGF-R).

Table for example 7. Characterization of first-pass EPCs cultured on plasma and anti-CD34 coated flasks

| Marker | Exp. #1 | Exp. #2 |
|---|---|---|
| CD45 | 85.34 | 97.10 |
| CD34 | 1.96 | 1.50 |
| CD117 | 0.64 | 0.83 |
| CD133 | 0.57 | 3.88 |
| KDR | 0.24 | 0.54 |

Example 8

In a set of separate experiments, enrichment of EPCs from first-pass cells was evaluated following in-vitro growth on Fibronectin-coated T-75 Flasks in the presence of medium containing autologous serum, VEGF and Heparin in a high % $CO_2$ humidified environment. Flow-cytometry percentage staining results from 3 independent experiments are summarized in the Table for example 8. These experiments were conducted with human blood, using the protocol described hereinabove. Before incubation the cells exhibited less than 1% CD34. 5-20% autologous serum (typically 10%), 1, 2, 10, or 20 ng/ml VEGF, 0.002-2 microgram/ml 17-β-Estradiol and 5-25 IU/ml Heparin that were incubated in 37° C., 6.5-12.5% $CO_2$ and 97% humidity are presented. The following surface markers were analyzed: CD45 (a pan-lymphocyte marker), the stem/progenitor cell marker CD34, and the EPC/endothelial cell marker CD133.

Table for example 8. Characterization of first-pass EPCs cultured in a humid environment containing hypercapnic conditions

| Marker | AVG | SE |
|---|---|---|
| CD45 | 90.47 | 4.53 |
| CD34 | 23.77 | 17.93 |
| CD133 | 4.48 | 2.10 |

Complete or partial loss of blood supply to body tissues (ischemia) is a common mechanism in many diseases either as a cause or as an intermediate stage responsible for the disease's outcome. This deficit in supply leads to the affected tissue becoming progressively incapable of performing its functions, to the onset of pathologic processes resulting from the deprivation of nutrients, mainly oxygen, as well as accumulation of metabolites, such as $CO_2$. If these processes are severe, they eventually lead to cell and tissue death.

The induction of new blood vessel formation to augment or replace the compromised blood supply leads to restoration of function of the affected tissue or organ, and prevention of death of the affected cells. The principle of restoring blood supply to a deprived organ is practiced by cardiologists (e.g., by coronary vessel graft surgery and balloon angioplasty) in order to restore the functioning of the heart and preventing further deterioration.

This invasive approach is generally possible only when large and medium sized vessels are occluded. However, in many diseases associated with a decrease in vascularization, the occlusion occurs in small vessels not amenable to this type of intervention.

In an embodiment of the present invention, EPCs are supplied to a blood-deprived organ or tissue in order to augment or replace the defective vascularization by creating new blood vessels in the deprived organ using autologous or non-autologous endothelial progenitor/stem cells injected either directly into the ischemic tissue, or into patent blood vessels in the proximity of the ischemic tissue. A successful creation of such vasculature generally restores the function, prevents further deterioration, forestalls the formation of pathological processes secondary to blood supply deprivation, and/or averts death of cells in the affected organ. Furthermore, in some cases, controlled blood vessel formation in certain regions of the organ reduce pathological vascularization of other regions within the organ that may reduce the organ's function.

In an embodiment of the present invention, supplying EPCs to an organ or tissue treats one or more of the following ischemia-related conditions. The resulting amelioration of the compromised blood supply generally partially or completely cures the disease or leads to cessation or slowing down of the progression of the condition.

Glaucoma. This disease consists of progressive death of optic nerve fibers associated with ischemia of the optic nerve head. A treatment leading to restoration of the optic nerve head vasculature generally arrests the disease process and restores some of the function of the optic nerve (at least in those optic nerve fibers whose cell bodies have not yet died, in spite of their axons being compromised at the nerve head). In an embodiment of the present invention, injecting EPCs into the optic nerve head and/or around it generally effects the desired vasculature induction. (See the above-mentioned article by Flammera J et al.)

Age-related macular degeneration. This disease is associated with circulatory disturbances in the choroid, the blood vessel tissue supplying the outer layers of the retina with its metabolic requirements. These disturbances compromise the retina, leading to its progressive death with consequent reduction in visual functions. In an embodiment of the present invention, injecting EPCs into the choroid generally arrests the disease process and prevents blindness. (See the above-mentioned article by Zarbin M A.)

Diabetic retinopathy. This disease is a small vessel disease that leads to local ischemia in the retina and therefore edema impairing vision. Although neovascularization occurs, it occurs as a result of ischemia, and it occurs in the region most important to accurate vision—the macula, thereby impairing vision. In an embodiment of the present invention, controlled induction of blood vessel growth by administration of EPCs to regions adjacent to, but not in, the macula reduces or eliminates vessel growth and edema formation in the macular area. This EPC-induced controlled induction of blood vessel growth typically supplies sufficient blood to the retina to obviate the retina's need to vascularize the macular area. (See the above-referenced article by Frank R N, and the above-referenced article by Singleton J R et al.)

Diabetic nephropathy. This disease involves atherosclerotic blockage of the kidney's blood vessels and destruction of the blood-filtering structures of the kidneys and thus kidney failure, which necessitates dialysis. In an embodiment of the present invention, induction of replacement vessels by injecting EPCs into the kidneys arrests the process. (See the above-referenced article by Bahlmann F H et al. (2004))

Non-union of bones. This occurrence after trauma and surgery usually results from insufficient blood supply in the fracture/surgical incision area of the affected bone. In an embodiment of the present invention, local application of EPCs to the fracture/surgical incision area of affected bone restores vascularization and enables healing of the lesion.

Chronic skin ulcers. These lesions are a result of compromised blood supply to the relevant area of the skin. In an embodiment of the present invention, local application of EPCs to chronic skin ulcers restores the blood supply and generally leads to healing of the wound.

Vascular dementia, post stroke. This condition results from progressive irreversible closure of blood vessels in the brain. In an embodiment of the present invention, supplying the brain with EPCs restores at least a portion of the compromised circulation and thus restores brain function and/or slows down deterioration of brain function.

Diabetic vasculopathy. This progressive occlusion of small vessels in the extremities is a common cause for surgical amputations. In an embodiment of the present invention, such amputations are prevented by restoring circulation in the affected limbs by local injection of EPCs.

Like all transplants, skin grafts depend on blood supply for survival (see, for example, the above-mentioned book edited by Greenfield, and the above-mentioned article by Kouwenhoven E A et al.). Both free grafts and skin flaps can fail because of inadequate vascularization. Free grafts require adequate vascularization in the bed, and flaps need the continuation of their own blood supply until local anastomoses can be established (see, for example, the above-mentioned articles by Browne E Z et al., Chen et al., and Beatrice et al.). This is also true for transplants made of artificial skin (see, for example, the above-mentioned article by Ferretti et al.). In these cases, good vascularization is a precondition for optimal reinnervation of the graft.

In an embodiment of the present invention, vascularization is induced by seeding skin grafts with EPCs. Such EPC-induced vascularization generally increases the likelihood of skin graft survival. For some applications, this EPC seeding technique is used in combination with techniques for endothelial cells transplantation described in the above-mentioned article by Schechner et al., mutatis mutandis.

In an embodiment of the present invention, vascularization is induced by seeding an attachment site with EPCs during reattachment of a severed limb. Such EPC seeding generally helps restore microcirculation to the reattached limb.

It is to be noted that the indications described hereinabove are only examples of the therapeutic uses of EPCs. In other embodiments of the present invention, other conditions in which blood circulation is compromised are treated by appropriate application of EPCs to locations which have insufficient or no blood vessels.

It is also noted that techniques described herein with respect to increasing stem cell populations prior to administration to heart patients may also be adapted for use with patients having any of the conditions described hereinabove.

An embodiment of the present invention comprises practicing a technique described in one or both of the following provisional patent applications (optionally in combination with a technique described herein):

(a) U.S. Provisional Patent Application 60/576,266, filed Jun. 1, 2004, entitled, "In vitro techniques for use with stem cells," and (b) U.S. Provisional Patent Application 60/588,520, filed Jul. 15, 2004, entitled, "Indications for stem cell use."

Both of these applications are assigned to the assignee of the present patent application, and are incorporated herein by reference.

Safety and efficacy of EPCs enriched from first-pass cells were evaluated in an ongoing clinical study. These experiments were conducted with patients' autologous blood, using the protocol described hereinabove.

Sixteen patients on maximal drug therapy suffering from severe angina pectoris have been enrolled in the clinical trial that was initiated by TheraVitae and performed in accordance with an embodiment of the present invention. The patients are followed for up to 6 months, as is normally done in cardiovascular clinical trials. Each patient constitutes his/her own control, with post-treatment condition being compared to the pre-treatment status. Some of the results of the first ten patients that have been followed for at least three months are presented below. It should be emphasized that the results presented herein are not complete and a thorough analysis of the data will be performed on completion of the clinical trial.

Safety—The treatment shows a high safety profile. A limited number of patients developed minor adverse events which were defined as possibly related to the therapy (elevated erythrocyte sedimentation rate, chest pain during angiography). These findings disappeared after a short period without affecting the patient's clinical condition.

Efficacy (see table 1, 2 and 3)—The general clinical condition of all of the patients improved, as shown by the improvement in the Canadian Cardiovascular Society Grading Scale for Angina Pectoris (CCS), showing better capacity to exercise. All patients improved their walking ability free of cardiac symptoms. This finding is also supported by the increase in estimated workload, an objective assessment of exercise capacity done by sestamibi scan. Both results show high statistical significance.

TABLE I

Patient clinical improvement as demonstrated by the Canadian Cardiovascular Society Grading Scale for Angina Pectoris (CCS).

|  | Mean value before treatment | Mean value after treatment | Mean percent improvement |
|---|---|---|---|
| CCS score | 1.92 | 1.00 | 52% |
| P value |  | 0.0029 |  |

TABLE II

Patient clinical improvement at 3 months, as demonstrated by 6-minute walk test

|  | Absolute Values | Percent |
|---|---|---|
| Total number of patients that improved | 10 | 100% |
| Improvement - average (meters) | 84 | 25% |
| P value | 0.0003 |  |

TABLE III

Patient improvement at 3 months, as demonstrated by the estimated workload (METs)

|  | Absolute Values | Percent |
|---|---|---|
| Number of patients that improved | 7 | 78% |
| Improvement - average | 1.42 | 20% |
| P value | 0.02 |  |

In an embodiment, EPCs produced by any of the techniques recited in any of the claims hereinbelow are administered to a human or animal.

In an embodiment, EPCs produced by any of the techniques recited in any of the claims hereinbelow are used in the treatment of a vessel and/or heart disorder, or to treat aging, or to treat a systemic disorder, or to treat a multi-system disorder.

For some applications, techniques described herein are applied to animal tissue.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with extracted blood, comprising:
applying blood to a first gradient suitable for selecting first-pass white blood cells having a density less than 1.077 g/ml;
applying the entire first-pass white blood cell fraction to a second gradient suitable for selecting second-pass cells having a density between 1.055 and 1.074 g/ml;
increasing the number of cells having a density between 1.055 and 1.074 g/ml, by culturing the second-pass cells for a period lasting between 1 and 30 days; and
identifying endothelial progenitor cells in the cultured cells.

2. The method according to claim 1, wherein culturing the second-pass cells comprises culturing the second-pass cells for a period lasting between 3 and 30 days.

3. The method according to claim 2, wherein applying the blood to the first gradient comprises applying the blood to a solution including a copolymer of sucrose and epichlorohydrin.

4. The method according to claim 2, wherein applying the first-pass cells to the second gradient comprises applying the first-pass cells to an aqueous solution of iodixanol.

5. The method according to claim 2, wherein applying the first-pass cells to the second gradient comprises applying the first-pass cells to a continuous density solution including polyvinylpyrrolidone-coated silica colloids.

6. The method according to claim 2 wherein increasing the number of cells comprises culturing the cells for a period lasting between 4 and 8 days.

7. The method according to claim 2, wherein culturing the second-pass cells comprises culturing the second-pass cells in a culture medium comprising one or more agents selected from the group consisting of: autologous serum, VEGF, b-FGF, IGF and heparin.

8. The method according to claim 2, further comprising, subsequently to the selecting of the first-pass cells, dividing the entire first-pass white blood cell fraction into respective first and second portions thereof, and wherein:
   applying the first pass-cells comprises applying the first portion of the first-pass white blood cells to the second gradient,
   the method further comprises mixing the second portion of the first-pass cells with the second-pass cells having the density of between 1.055 and 1.074 g/ml, and
   increasing the number of cells comprises increasing the number of cells following the mixing.

9. The method according to claim 8, wherein dividing the first-pass cells comprises setting the first portion to be larger than the second portion.

10. The method according to claim 8, wherein dividing the first-pass cells comprises setting the first portion to be smaller than the second portion.

\* \* \* \* \*

UNITED STATES PATENT AND TRADEMARK OFFICE
CERTIFICATE OF CORRECTION

PATENT NO.       : 8,685,724 B2                                              Page 1 of 1
APPLICATION NO. : 11/628488
DATED            : April 1, 2014
INVENTOR(S)      : Fulga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1488 days.

Signed and Sealed this

Twenty-ninth Day of September, 2015

Michelle K. Lee
*Director of the United States Patent and Trademark Office*